(12) United States Patent
Bogle et al.

(10) Patent No.: US 7,265,119 B2
(45) Date of Patent: Sep. 4, 2007

(54) TARTRATE SALTS OF 5,8,14-TRIAZATETRACYCLO[10.3.1.0$^{2,11}$.0$^{4,9}$]-HEXADECA-2(11),3,5,7,9-PENTAENE AND PHARMACEUTICAL COMPOSITIONS THEREOF

(75) Inventors: David E. Bogle, Jewett City, CT (US); Glenn R. Williams, Oaksville (CA); Peter R. Rose, Ledyard, CT (US)

(73) Assignee: Pfizer Inc, New York, NY (US)

( * ) Notice: Subject to any disclaimer, the term of this patent is extended or adjusted under 35 U.S.C. 154(b) by 105 days.

(21) Appl. No.: 11/069,724

(22) Filed: Feb. 28, 2005

(65) Prior Publication Data

US 2005/0148591 A1    Jul. 7, 2005

Related U.S. Application Data

(63) Continuation of application No. 10/139,730, filed on May 6, 2002, now Pat. No. 6,890,927.

(60) Provisional application No. 60/290,861, filed on May 14, 2001.

(51) Int. Cl.
C07D 241/36    (2006.01)
A61K 31/50    (2006.01)
A61K 31/495    (2006.01)

(52) U.S. Cl. .................... 514/250; 544/343
(58) Field of Classification Search ............... 544/343; 514/250
See application file for complete search history.

(56) References Cited

U.S. PATENT DOCUMENTS 3,471,503 A    10/1969    Carson

FOREIGN PATENT DOCUMENTS

| EP | 1078637 | 2/2001 |
|---|---|---|
| WO | WO 9935131 | 7/1999 |

OTHER PUBLICATIONS

Paul H. Mazzochi, et al., "Synthesis and Pharmacological Activity of 2,3,4,5-Tetrahydro-1,5-Methano-1H-3-Benzazepines", J. Med. Chem., vol. 22, No. 4, 1979, pp. 455-457, XP002090422.

*Primary Examiner*—Bruck Kifle
(74) *Attorney, Agent, or Firm*—Steve T. Zelson; A. David Joran

(57) ABSTRACT

The present invention is directed to the tartrate salts of 5,8,14-triazatetracyclo[10.3.1.0$^{2,11}$.0$^{4,9}$]-hexadeca-2(11),3,5,7,9-pentaene:

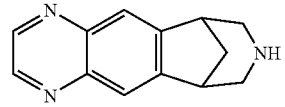

and pharmaceutical compositions thereof. The present invention in particular is directed to the L-tartrate salt, and further to the various polymorphs of the L-tartrate salt, including two distinct anhydrous polymorphs (referred to herein as Forms A and B) and a hydrate polymorph (referred to herein as Form C). In addition, the present invention is also directed to the D-tartrate salt of 5,8,14-triazatetracyclo[10.3.1.0$^{2,11}$.0$^{4,9}$]-hexadeca-2(11),3,5,7,9-pentaene and the various polymorphs thereof; as well as the D,L-tartrate salt thereof and its polymorphs, and the meso-tartrate salt thereof and its polymorphs.

15 Claims, 20 Drawing Sheets

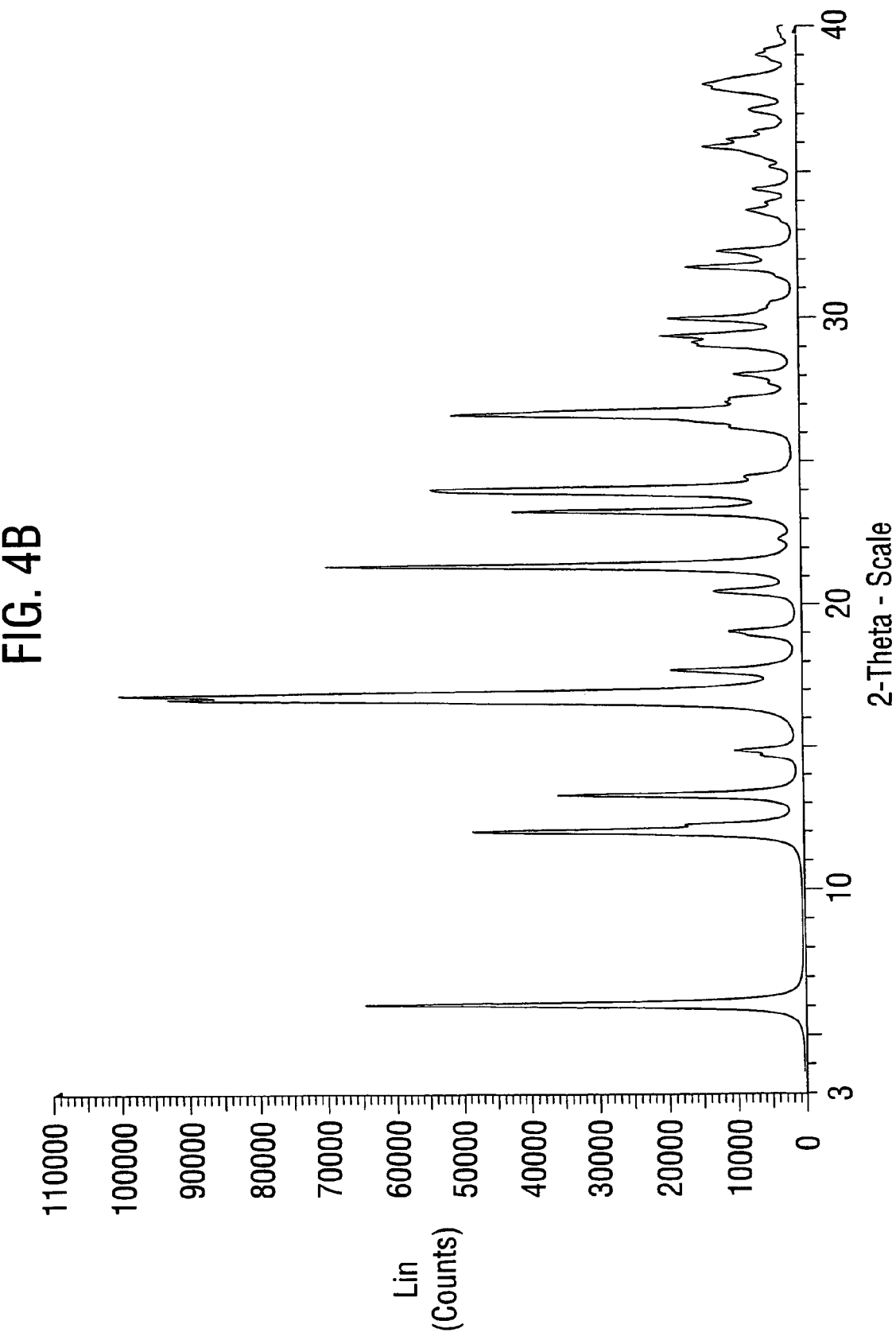

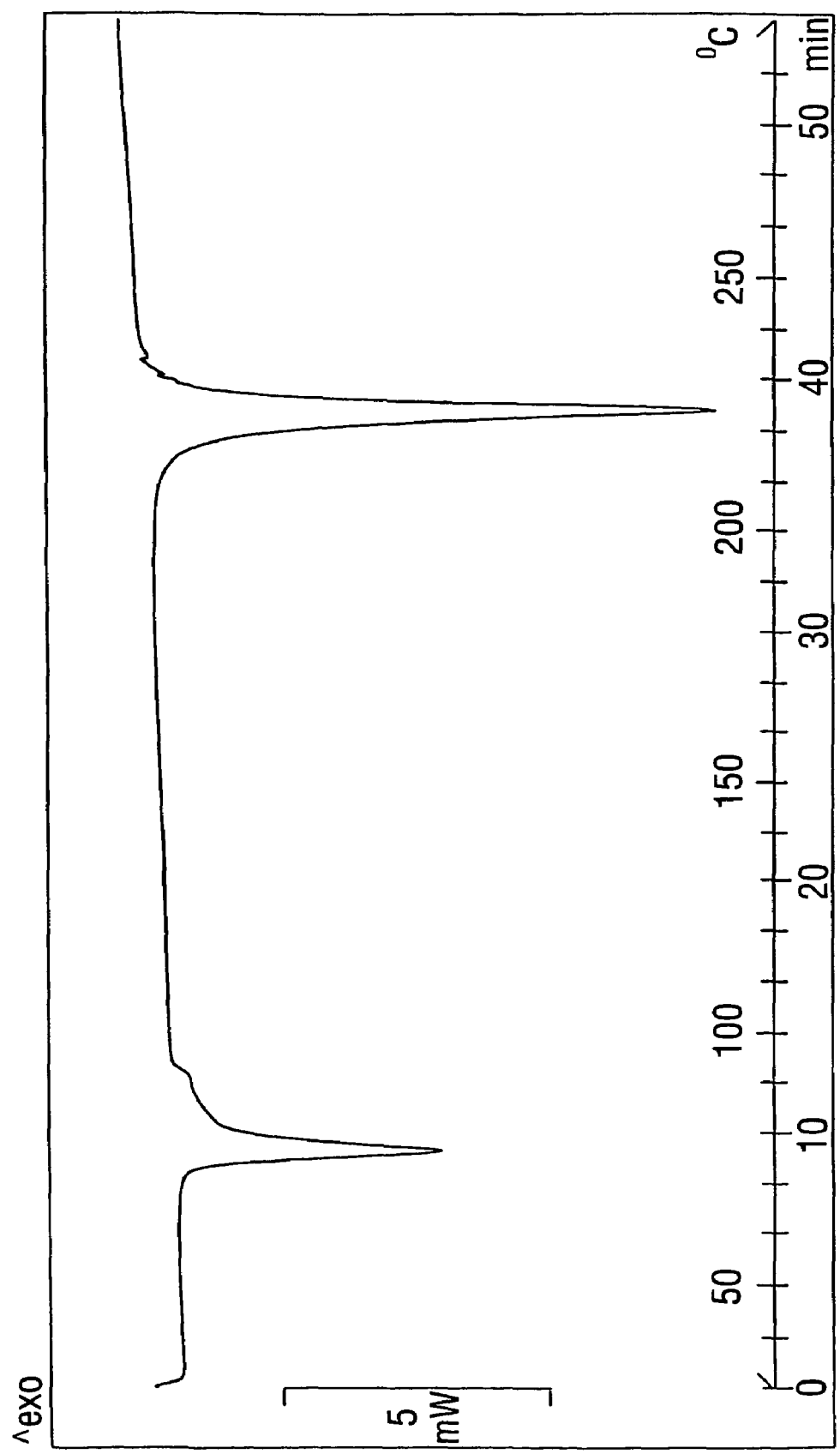

TARTRATE SALTS OF 5,8,14-TRIAZATETRACYCLO[10.3.1.0$^{2,11}$.0$^{4,9}$]-HEXADECA-2(11),3,5,7,9-PENTAENE AND PHARMACEUTICAL COMPOSITIONS THEREOF

This application is a continuation of U.S. Ser. No. 10/139,730, filed May 6, 2002 now U.S. Pat. No. 6,890,927, which claims the benefit of U.S. Provisional Application Ser. No. 60/290,861, filed May 14, 2001.

The present invention is directed to the tartrate salts of 5,8,14-triazatetracyclo[10.3.1.0$^{2,11}$.0$^{4,9}$]-hexadeca-2(11),3,5,7,9-pentaene:

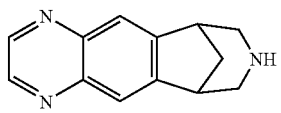

and pharmaceutical compositions thereof. The present invention in particular is directed to the L-tartrate salt, and further to the various polymorphs of the L-tartrate salt, including two distinct anhydrous polymorphs (referred to herein as Forms A and B) and a hydrate polymorph (referred to herein as Form C). In addition, the present invention is also directed to the D-tartrate salt of 5,8,14-triazatetracyclo[10.3.1.0$^{2,11}$.0$^{4,9}$]-hexadeca-2(11),3,5,7,9-pentaene and the various polymorphs thereof; as well as the D,L-tartrate salt thereof and its polymorphs, and the meso-tartrate salt thereof and its polymorphs.

The compound, 5,8,14-triazatetracyclo[10.3.1.0$^{2,11}$.0$^{4,9}$]-hexadeca-2(11),3,5,7,9-pentaene, binds to neuronal nicotinic acetylcholine specific receptor sites and is useful in modulating cholinergic function. This compound is useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy.

The tartrate salts of this invention may also be used in a pharmaceutical composition in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Compounds that bind to neuronal nicotinic receptor sites, including 5,8,14-triazatetracyclo[10.3.1.0$^{2,11}$.0$^{4,9}$]-hexadeca-2(11),3,5,7,9-pentaene, and its hydrochloride salt, are referred to in WO 99135131, published Jul. 15, 1999 (corresponding to U.S. Ser. No. 09/402,010, filed Sep. 28, 1999 and U.S. Pat. No. 09/514,002, filed Feb. 25, 2000). The foregoing applications, owned in common with the present application and incorporated herein by reference in their entirety, generically recite pharmaceutically acceptable add addition salts for the compounds referred to therein.

The L-tartrate salt of the present invention exhibits properties, including those of high solid-state stability and compatibility with certain drug product formulation excipients, that render it superior to previously known salts of 5,8,14-triazatetracyclo[10.3.1.0$^{2,11}$.0$^{4,9}$]-hexadeca-2(11),3,5,7,9-pentaene. Further, the D-tartrate and D,L-tartrate salts exhibit properties that also make them appropriate for drug product formulation use.

BRIEF DESCRIPTION OF THE DRAWINGS

FIG. 4B is the calculated powder X-ray diffraction pattern of the Form C L-tartrate salt hydrate of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

FIGS. 9A, 9B and 9C are the differential scanning calorimetric traces for the L-tartrate salts Forms A, B and C, respectively, of 5,8,14-triazatetra-cyclo[10.3.1.0$^{2,11}$.0$^{4,9}$]-hexadeca-2(11),3,5,7,9-pentaene.

SUMMARY OF THE INVENTION

The present invention relates to the tartrate salts of 5,8,14-triazatetracyclo[10.3.1.0$^{2,11}$.0$^{4,9}$]-hexadeca-2(11),3,5,7,9-pentaene. The tartrate salts of the invention include the L-tartrate, D-tartrate, D,L-tartrate and meso-tartrate salts.

In particular, the present invention relates to the L-tartrate salt of 5,8,14-triazatetracyclo[10.3.1.0$^{2,11}$.0$^{4,9}$]-hexadeca-2(11),3,5,7,9-pentaene.

In one embodiment of the invention, the L-tartrate of 5,8,14-triazatetracyclo[10.3.1.0$^{2,11}$.0$^{4,9}$]-hexadeca-2(11),3,5,7,9-pentaene is the anhydrous L-tartrate salt, referred to herein as Form A. The L-tartrate Form A is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 6.1 | 14.5 |
| 12.2 | 7.2 |
| 13.0 | 6.8 |
| 14.7 | 6.0 |
| 16.8 | 5.3 |

-continued

| Angle 2θ (±0.2) | d-value (Å) (±0.2) |
|---|---|
| 19.4 | 4.6 |
| 21.9 | 4.1 |
| 24.6 | 3.6 |

The L-tartrate crystal Form A is characterized in that it has a onset of melt at about 223° C. as measured by differential scanning calorimetry at a heating rate of 5 degrees per minute. The L-tartrate Form A is also characterized in that when examined by solid state $^{13}$C NMR cross-polarization magic angle spinning techniques, it exhibits the following principal resonance peaks (±0.1 ppm) downfield from 100 ppm (adamantane standard 29.5 ppm): 178.4, 149.3, 147.4, 145.1, and 122.9 ppm.

In another embodiment of the invention, the L-tartrate of 5,8,14-triazatetracyclo[10.3.1.0$^{2,11}$.0$^{4,9}$]-hexadeca-2(11),3,5,7,9-pentaene is another anhydrous L-tartrate salt polymorph, referred to herein as Form B. The L-tartrate salt Form B is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 5.9 | 15.0 |
| 12.8 | 6.9 |
| 14.4 | 6.1 |
| 15.3 | 5.8 |
| 16.9 | 5.2 |
| 17.2 | 5.2 |
| 21.8 | 4.1 |
| 23.8 | 3.7 |
| 25.1 | 3.5 |

Figure 8A:
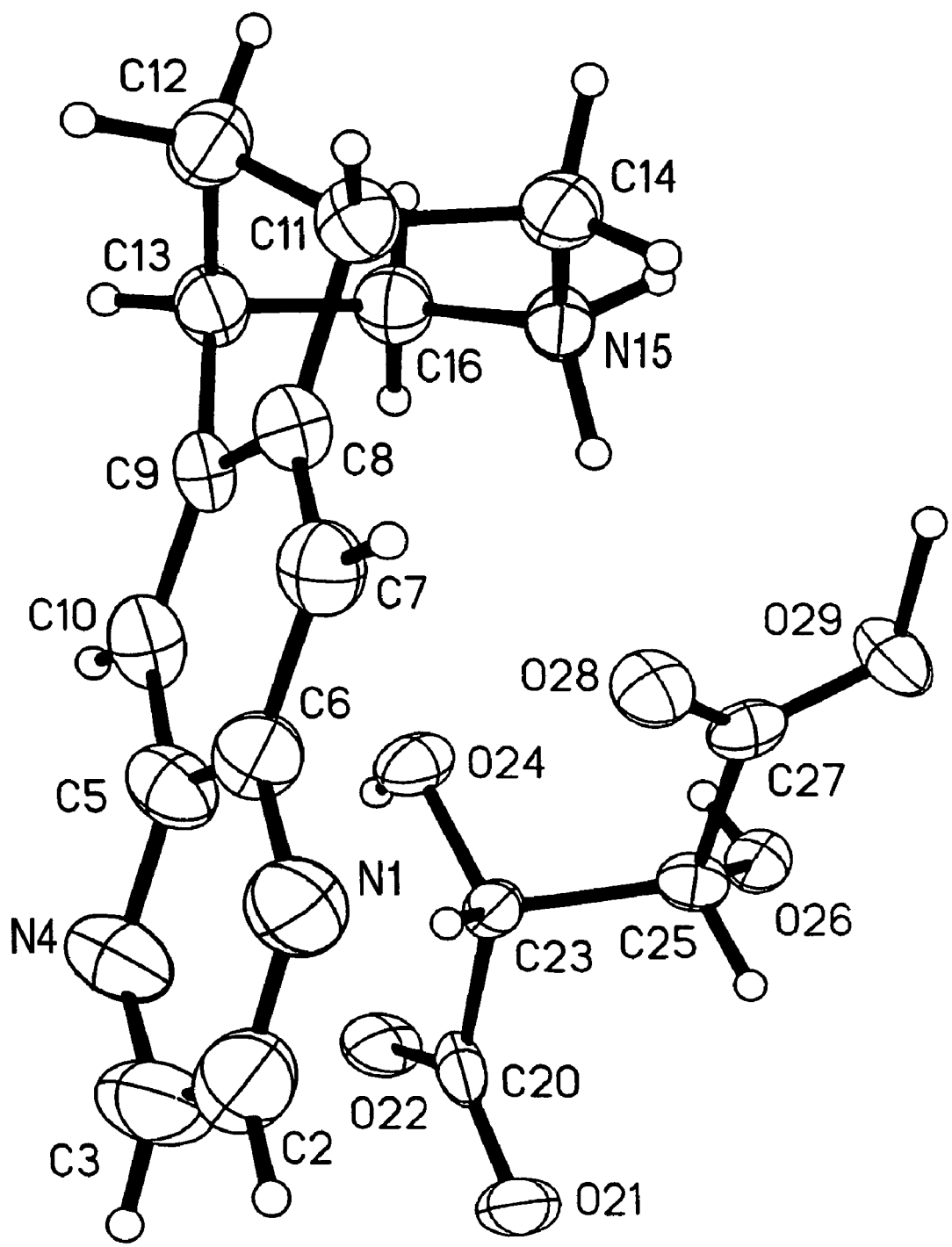
FIG. 8A is the X-ray crystal structure (absolute configuration) for the anhydrous Form B L-tartrate salt of 5,8,14-triazatetra-cyclo[10.3.1.0$^{2,11}$.0$^{4,9}$]-hexadeca-2(11),3,5,7,9-pentaene.

The L-tartrate salt Form B has a single crystal x-ray structure (absolute configuration) as set forth in FIG. 8A. Further, the Form B forms orthorhombic crystals belonging to the P2(1)2(1)2(1) space group. Form B is further characterized in having an onset of melting at about 215° C. as measured by differential scanning calorimetry at a heating rate of 5 degrees per minute. Further, Form B of the invention is also characterized in having an aqueous solubility of about 156 mg/ml and a native pH of about 3.3 in aqueous solution. In addition, Form B has a hygroscopicity of approximately 0.2% at 90% relative humidity.

The L-tartrate Form B is also characterized in that when examined by solid state $^{13}$C NMR cross-polarization magic angle spinning techniques, it exhibits the following principal resonance peaks (±0.1 ppm) downfield from 100 ppm (adamantane standard 29.5 ppm): 179.2, 178.0, 147.4, 145.2, 144.4, 124.8 and 122.5 ppm.

In another embodiment of the invention, the L-tartrate of 5,8,14-triazatetracyclo[10.3.1.0$^{2,11}$.0$^{4,9}$]-hexadeca-2(11),3,5,7,9-pentaene is the hydrate L-tartrate salt, referred to herein as Form C. The L-tartrate Form C is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
| --- | --- |
| 5.9 | 15.1 |
| 11.8 | 7.5 |
| 16.5 | 5.4 |
| 21.2 | 4.2 |
| 23.1 | 3.8 |
| 23.8 | 3.7 |
| 26.5 | 3.4 |

Figure 8B:
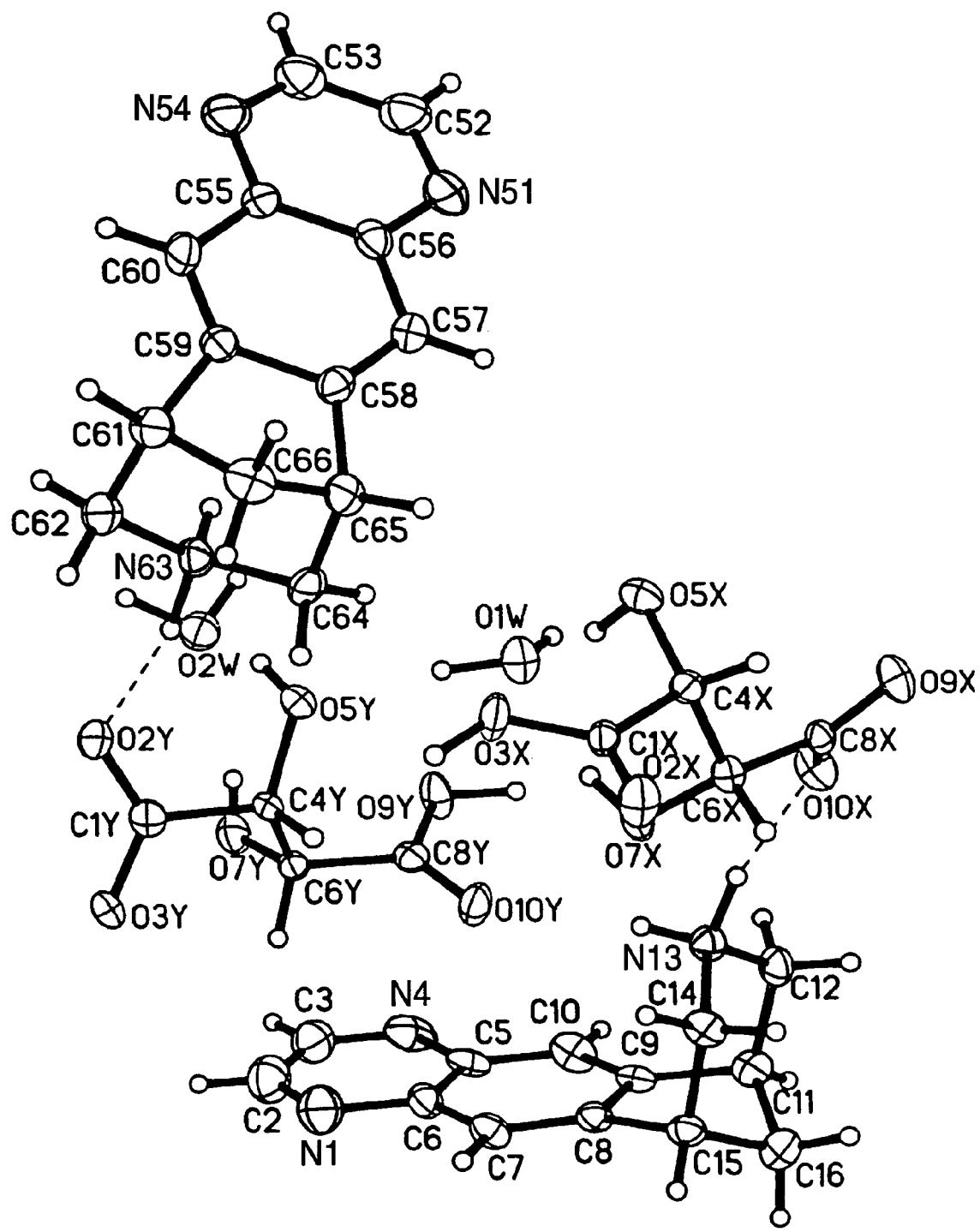
FIG. 8B is the X-ray crystal structure (absolute configuration) for the Form C L-tartrate salt hydrate of 5,8,14-triazatetra-cyclo[10.3.1.0$^{2,11}$.0$^{4,9}$]-hexadeca-2(11),3,5,7,9-pentaene.

The hydrate L-tartrate crystal Form C has a single crystal structure as set forth in FIG. 8B. Further, the hydrate Form C forms monoclinic crystals belonging to the P2(1) space group. Form C is further characterized in having an onset of a solid-solid transition at about 72° C. and an onset of melting transition at about 220° C. Because Form B converts to the hydrate Form C upon contact with 100% relative humidity, Form C has the same aqueous solubility as Form B.

The L-tartrate Form C is also characterized in that when examined by solid state $^{13}$C NMR cross-polarization magic angle spinning techniques, it exhibits the following principal resonance peaks (±0.1 ppm) downfield from 100 ppm (adamantane standard 29.5 ppm): 179.0, 176.1, 147.5, 144.5 and 124.6 ppm.

A further embodiment of the invention is directed to the D-tartrate salt of 5,8,14-triazatetracyclo[10.3.1.0$^{2,11}$.0$^{4,9}$]-hexadeca-2(11),3,5,7,9-pentaene. In particular, the present invention is directed to the three D-tartrate salt polymorphs (referred to here as Forms A', B' and C') which exhibit the same x-ray diffraction characteristics, hygroscopicity, water content and thermal characteristics as Forms A, B and C of the L-tartrate salt.

In another embodiment, the present invention relates to the D,L-tartrate salt of 5,8,14-triazatetracyclo[10.3.1.0$^{2,11}$.0$^{4,9}$]-hexadeca-2(11),3,5,7,9-pentaene, and in particular, two polymorphs, an anhydrous form (herein referred to as Form X) and a hydrate form (herein referred to as Form Y).

The D,L-tartrate Form X is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
| --- | --- |
| 6.0 | 14.6 |
| 11.9 | 7.4 |
| 15.0 | 5.9 |
| 17.1 | 5.2 |
| 22.1 | 4.0 |
| 24.5 | 3.6 |

The D,L-tartrate Form X is further characterized in having an onset of a melting transition at about 212° C.

The D,L-tartrate Form Y is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
| --- | --- |
| 6.2 | 14.2 |
| 12.0 | 7.4 |
| 15.2 | 5.8 |
| 18.1 | 4.9 |
| 24.0 | 3.7 |
| 25.1 | 3.5 |

The D,L-tartrate Form Y is further characterized in having an onset of a solid-solid transition at about 131° C. and an onset of melting transition at about 217° C.

Another embodiment of the invention relates to a pharmaceutical composition comprising at least one of polymorphic Forms A, B or C, preferably Form B, of the L-tartrate salt of 5,8,14-triazatetracyclo[10.3.1.0$^{2,11}$.0$^{4,9}$]-hexadeca-2(11),3,5,7,9-pentaene and a pharmaceutically acceptable carrier or excipient, for use in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchits, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), and Tourette's Syndrome. Another more preferred embodiment of the invention is wherein the pharmaceutical composition is useful in the treatment of nicotine dependency, addiction and withdrawal; most preferably, for use in smoking cessation therapy.

The present invention further relates to pharmaceutical compositions for the uses described in the foregoing paragraph comprising any one of the D-tartrate salt of, the D,L-tartrate salt of, or the meso-tartrate salt of 5,8,14-triazatetracyclo[10.3.1.0$^{2,11}$.0$^{4,9}$]-hexadeca-2(11),3,5,7,9-pentaene.

The present invention further relates to a method of treating inflammatory bowel disease (including but not limited to ulcerative colitis, pyoderma gangrenosum and Crohn's disease), irritable bowel syndrome, spastic dystonia, chronic pain, acute pain, celiac sprue, pouchits, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), and Tourefte's Syndrome comprises administering to a subject in need of treatment a therapeutically effective amount of any of Forms A, B or C of the L-tartrate salt of 5,8,14-triazatetracyclo[10.3.1.0$^{2,11}$.0$^{4,9}$]-hexadeca-2(11),3,5,7,9-pentaene, preferably Form B. Another more preferred embodiment of the invention relates to a method of treatment for nicotine dependency, addiction and withdrawal, in particular for use in smoking cessation therapy activity, comprising the administration of any of Forms A, B or C of the L-tartrate salt of 5,8,14-triazatetracyclo[10.3.1.0$^{2,11}$.0$^{4,9}$]-hexadeca-2(11),3,5,7,9-pentaene, preferably Form B, to a subject in need thereof.

The present invention further relates to methods of treatment described in the foregoing paragraph comprising the administration of any of the D-tartrate salt, the D,L-tartrate salt or the meso-tartrate salt of 5,8,14-triazatetracyclo[10.3.1.0$^{2,11}$.0$^{4,9}$]-hexadeca-2(11),3,5,7,9-pentaene to a subject in need thereof.

The term "treating" as used herein, refers to, and includes, reversing, alleviating, inhibiting the progress of, or preventing a disease, disorder or condition, or one or more symptoms thereof; and the term "treatment" refers to the act of treating, as defined above.

The invention also relates to a process for the preparation of the Form A of L-tartrate salt of 5,8,14-triazatetracyclo[10.3.1.0$^{2,11}$.0$^{4,9}$]-hexadeca-2(11),3,5,7,9-pentaene comprising the steps of
  (i) contacting 5,8,14-triazatetracyclo[10.3.1.0$^{2,11}$.0$^{4,9}$]-hexadeca-2(11),3,5,7,9-pentaene in a suitable solvent with between 1 and 2 equivalents of L-tartaric acid; and
  (ii) collecting the crystals formed.

A preferred embodiment of this invention relates to the above process wherein 1.1 equivalents of L-tartaric acid is employed and the tartaric acid is added to a solution containing the free base. A preferred mode of practicing this process is wherein the contact step is allowed to proceed for less than 2 hours. A more preferred embodiment of this invention relates to the above process wherein the contact step (i.e., step "(i)" above) is allowed to proceed above 45° C. Another preferred embodiment of this invention relates to the above process wherein the suitable solvent is selected from the group consisting of a ($C_1$-$C_6$)alkyl alcohol, a ($C_1$-$C_6$)alkyl ketone or a ($C_1$-$C_6$)alkyl ether, acetonitrile and ($C_1$-$C_6$)alkyl esters (e.g., ethyl acetate, isopropyl acetate, etc.). More preferably, the suitable solvent is ethanol or methanol.

The invention further relates to a process for the preparation of Form A' of the D-tartrate salt comprising steps (i) and (ii) referred to above for making Form A of the L-tartrate salt, but using D-tartaric acid in step (i) in place of L-tartaric acid.

The invention also relates to a process for the preparation of Form B of L-tartrate salt of 5,8,14-triazatetracyclo[10.3.1.0$^{2,11}$.0$^{4,9}$]-hexadeca-2(11),3,5,7,9-pentaene comprising the steps of:
  (i) contacting 5,8,14-triazatetracyclo[10.3.1.0$^{2,11}$.0$^{4,9}$]-hexadeca-2(11),3,5,7,9-pentaene in a suitable solvent with about 1 to about 2.3 equivalents of L-tartaric acid; and
  (ii) collecting the crystals formed.

A preferred embodiment of this invention relates to the above process wherein about 1.1 to about 2.2 equivalents, more preferably 1.1 equivalents, of L-tartaric acid is employed and the free base in solution is added to a solution containing L-tartaric acid. A preferred mode of practicing this process is wherein the contact step is allowed to proceed for a minimum of 1 hours; more preferably, for at least 2 hours; most preferably, longer than 12 hours. A preferred embodiment is wherein the suitable solvent is selected from the group consisting of a ($C_1$-$C_6$)alkyl alcohol, a ($C_1$-$C_6$) alkyl ketone or a ($C_1$-$C_6$)alkyl ether, acetonitrile and ($C_1$-$C_6$)alkyl esters (e.g., ethyl acetate, isopropyl acetate, etc.). More preferably, the suitable solvent is methanol or ethanol, most preferably methanol.

The invention further relates to a process for the preparation of Form B' of the D-tartrate salt comprising steps (i) and (ii) referred to above for making Form B of the L-tartrate salt, but using D-tartaric acid in step (i) in place of L-tartaric acid.

Another aspect of the present invention relates to a process for the preparation of the Form C of the L-tartrate salt of 5,8,14-triazatetracyclo[10.3.1.0$^{2,11}$.0$^{4,9}$]-hexadeca-2(11),3,5,7,9-pentaene comprising the steps of:
  (i) contacting either of Form A or Form B of the L-tartrate salt of 5,8,14-triazatetracyclo[10.3.1.0$^{2,11}$.0$^{4,9}$]-hexadeca-2(11),3,5,7,9-pentaene with water; and
  (ii) collecting the crystals formed.

A preferred embodiment of this invention relates to the above process wherein the contacting of step (i) comprises slurrying either of Forms A or B with water with subsequent addition of an organic solvent to promote precipitation of the Form C product. A more preferred embodiment of the process is wherein the organic solvent use to promote precipitation is methanol, ethanol or acetonitrile.

The invention further relates to a process for the preparation of Form C' of the D-tartrate salt comprising steps (i) and (ii) referred to above for making Form C of the L-tartrate salt but using Forms A' or B' of the D-tartrate salt in step (i) in place of Forms A or B of the L-tartrate salt.

The present invention further relates to a process for the preparation of Form X of the D,L-tartrate salt of 5,8,14-triazatetracyclo[10.3.1.0$^{2,11}$.0$^{4,9}$]-hexadeca-2(11),3,5,7,9-pentaene comprising the steps of:
  (i) contacting 5,8,14-triazatetracyclo[10.3.1.0$^{2,11}$.0$^{4,9}$]-hexadeca-2(11),3,5,7,9-pentaene in a suitable solvent with about 1 to about 2.3 equivalents of D,L-tartaric acid; and
  (ii) collecting the crystals formed.

A preferred embodiment of this invention relates to the above process wherein about 2.2 equivalents of D,L-tartaric acid is employed and the free base in solution is added to a solution containing D,L-tartaric acid. A preferred mode of practicing this process involves allowing the contact step to proceed for a minimum of 2 hours; more preferably, for at least 12 hours; and most preferably, at least 24 hours.

Another preferred embodiment of this invention relates to the above process for preparing Form X wherein the suitable solvent is anhydrous or nearly anhydrous and is selected from the group consisting of a $(C_1$-$C_6)$alkyl alcohol, a $(C_1$-$C_6)$alkyl ketone or a $(C_1$-$C_6)$alkyl ether, acetonitrile and $(C_1$-$C_6)$alkyl esters (e.g., ethyl acetate, isopropyl acetate, etc.). More preferably, the suitable solvent is ethanol.

The present invention further relates to a process for the preparation of Form Y of the D,L-tartrate salt of 5,8,14-triazatetracyclo[10.3.1.0$^{2,11}$.0$^{4,9}$]-hexadeca-2(11),3,5,7,9-pentaene comprising the steps of:

(i) contacting 5,8,14-triazatetracyclo[10.3.1.0$^{2,11}$.0$^{4,9}$]-hexadeca-2(11),3,5,7,9-pentaene in a suitable solvent with about 1 to about 2.3 equivalents of D,L-tartaric acid; and (ii) collecting the crystals formed.

A preferred embodiment of this invention relates to the above process wherein about 2.2 equivalents of D,L-tartaric acid is employed and the free base in solution is added to a solution containing D,L-tartaric acid. A preferred mode of practicing this process involves allowing the contact step to proceed for a minimum of 2 hours; more preferably, for at least 12 hours; most preferably, for at least 24 hours.

Another preferred embodiment of this invention relates to the above process for preparing Form Y wherein the suitable solvent is selected from the group consisting of a $(C_1$-$C_6)$ alkyl alcohol, a $(C_1$-$C_6)$alkyl ketone or a $(C_1$-$C_6)$alkyl ether, acetonitrile and $(C_1$-$C_6)$alky esters (e.g., ethyl acetate, isopropyl acetate, etc.) admixed with water. More preferably, the suitable solvent is ethanol admixed with water; most preferably, 20% aqueous ethanol.

DETAILED DESCRIPTION OF THE INVENTION

The compound, 5,8,14-triazatetracyclo[10.3.1.0$^{2,11}$.0$^{4,9}$]-hexadeca-2(11),3,5,7,9-pentaene is a nicotinic partial agonist for the treatment of a number of CNS diseases, disorders and conditions including, in particular, nicotine dependency, addiction and withdrawal.

Although in general the salts of 5,8,14-triazatetracyclo[10.3.1.0$^{2,11}$.0$^{4,9}$]-hexadeca-2(11),3,5,7,9-pentaene are all crystalline, the majority of such salts are so significantly hygroscopic as to render them poor candidates for pharmaceutical formulation use. The L-tartrate salt of 5,8,14-triazatetracyclo[10.3.1.0$^{2,11}$.0$^{4,9}$]-hexadeca-2(11),3,5,7,9-pentaene is very slightly hygroscopic, has high aqueous solubility and is high melting. These characteristics, combined with its relative inertness towards common excipients, make it highly suitable for pharmaceutical formulation use. The D-tartrate salt, the D,L-tartrate salt and the meso-tartrate salt of 5,8,14-triazatetracyclo[10.3.1.0$^{2,11}$.0$^{4,9}$]-hexadeca-2(11),3,5,7,9-pentaene also exhibit favorable characteristics.

The L-tartrate salt exists as three possible forms: two anhydrous forms and one hydrate form. Of the two anhydrous forms, Form A and Form B, Form A is the kinetic polymorph, which will convert under appropriate conditions to the thermodynamically favored Form B. The hydrate L-tartrate salt Form C is a monohydrate and is relatively stable under ambient conditions. It will maintain its one equivalent of water under vacuum at moderate temperatures for at least a day (e.g., for 24 hours in a 45° C. vacuum oven), but eventually over time (i.e., 48 hours or more) will lose water and convert to the anhydrous Form B. Form B is the most stable of the polymorphs at low humidity. Accordingly, Form B would appear to be the most appropriate and most stable polymorph of the L-tartrate salts of 5,8,14-triazatetracyclo[10.3.1.0$^{2,11}$.0$^{4,9}$]-hexadeca-2(11),3,5,7,9-pentaene for pharmaceutical formulation use.

As noted above, Form A is the anhydrous kinetic polymorph, which converts under appropriate conditions to the thermodynamically-favored Form B. Form A is obtainable from a synthesis involving, e.g., contacting the free base of 5,8,14-triazatetracyclo[10.3.1.0$^{2,11}$.0$^{4,9}$]-hexadeca-2(11),3,5,7,9-pentaene with approximately one equivalent of L-tartaric acid in methanol or ethanol, allowing little or no time for equilibration. Form A is observed as the resulting product initially from the combination of the 5,8,14-triazatetracyclo [10.3.1.0$^{2,11}$.0$^{4,9}$]-hexadeca-2(11),3,5,7,9-pentaene free base and L-tartaric acid, but Form B begins to form on continued or prolonged agitation of the reaction mixture. The rate of formation of Form B may be accelerated by using at least a two-fold or more stoichiometric excess of L-tartaric acid (i.e., faster with 2.2 equivalents of L-tartaric acid present than with only 1.1 equivalents) and allowing the reaction to proceed for longer than two hours, preferably for at least a day or more. Conversion to Form B is ordinarily complete after about 5 hours using 2.2 equivalents. In contrast, the conversion may require more than 20 hours using 1.1 equivalents. In any case, conversion to Form B is usually complete under most conditions after 48 hours at 20-25° C.

The temperature of the L-tartrate salt formation reaction also influences whether Form A or Form B is isolated, since Forms A and B appear to be thermally interconvertable. Running the salt formation reaction above 45° C. give Form A. Conversely, formation of the salt below 45° C. results in the formation of predominantly Form B. Also, stirring Form A in methanol below 40° C. results in the formation of Form B.

Although any number of solvents may be used, including most lower alcohols, Form B is obtained in high yield preferably using methanol, which permits a high filtration rate of the crystalline material and allows the formation of Form B directly. The solubility of both the free base and L-tartaric acid are higher in methanol than in other lower alkyl alcohols.

The rate of formation of Form B may also be accelerated by employing the specific order of addition wherein the 5,8,14-triazatetracyclo[10.3.1.0$^{2,11}$.0$^{4,9}$]-hexadeca-2(11),3,5,7,9-pentaene free base is added to the solution of L-tartaric acid. To maximize the virtual concentration of L-tartaric acid present in the reaction, the methanolic solution of free base may be added to a solution containing either 1.1 or more equivalents of L-tartaric add at 20° C. The desired anhydrous Form B may then be isolated directly and the polymorph conversion completed in less than 2 hours.

One optimized procedure for making the anhydrous Form B comprises charging a speck-free vessel with between 1.1 and 2.2 equivalents of L-tartaric add and methanol (4 to 50 volumes), and stirring this mixture until dissolved and speck-free filtering the resulting solution into a crystallization vessel. 5,8,14-triazatetracyclo[10.3.1.0$^{2,11}$.0$^{4,9}$]-hexadeca-2(11),3,5,7,9-pentaene free base (1.0 equivalents) and methanol (4 to 50 volumes) are stirred in a vessel until dissolved at 0 to 50° C., more preferably at 20 to 25° C. The resulting solution of 5,8,14-triazatetracyclo[10.3.1.0$^{2,11}$.0$^{4,9}$]-hexadeca-2(11),3,5,7,9-pentaene free base is then added over about a period of time ranging from 1 minute to 2 hours, more preferably over about 30 minutes, to the L-tartaric acid solution. The product was allowed to stir at 0 to 40° C., more preferably at 20 to 25° C., for between 1 and 48 hours, more preferably for about 1 hour, and then isolated by filtration. The product is dried generally under vacuum at 20 to 60° C., more preferably at 35 to 45° C., to give Form B of the L-tartrate salt of 5,8,14-triazatetracyclo[10.3.1.0$^{2,11}$.0$^{4,9}$]-hexadeca-2(11),3,5,7,9-pentaene.

Both anhydrous Forms A and B can be converted to the monohydrate Form C by exposing either to a relative humidity (RH) of 100% or slurrying either of them in water. Form C is most readily obtained from either of Forms A or B by dissolving either in water at 20 to 50° C. followed by addition of an organic solvent in which the salt is not soluble, preferably methanol, ethanol or acetonitrile, and allowing the mixture to stir for between 1 and 30 minutes, preferably about 10 minutes. Upon filtering off the Form C which precipitates out as a white salt, the Form C salt may be air dried.

Noteworthy is that when exposed to conditions of 100% RH, Form B will convert to Form C within 2 days. Conversely, however, Form C readily converts to Form B upon exposure to 0% relative humidity conditions in roughly the same period of time. Hydrate Form C will however more slowly dehydrate upon exposure to conditions of less than 50% RH. Experiments at 23% and 43% RH have verified this phenomena. Nonetheless, both Forms B and C appear to be relatively stable over a several month period at RH greater than 60%, as experiments at 75% and 87% relative humidity have shown.

Further, Form A can be obtained from Form C by dissolving Form C in a hot organic solvent, preferably ethanol, at or near its reflux point, preferably at about 75° C., and allowing it to stir for from 10 minutes to 3 hours, preferably 30 minutes. Hot filtering the mixture allows the collection of crystals which upon drying in a vacuum oven at 45° C. yields Form A.

The D-tartrate salt of 5,8,14-triazatetracyclo[10.3.1.0$^{2,11}$.0$^{4,9}$]-hexadeca-2(11),3,5,7,9-pentaene has three polymorphs (Forms A', B' and C'), which exhibit the same x-ray diffraction characteristics, hygroscopicity, water content and thermal characteristics as the corresponding Forms A, B and C, respectively, of the L-tartrate salt; and are made in an identical manner as the corresponding L-tartrate salt polymorphs, with the exception that D-tartaric acid is employed in those procedures in place of L-tartaric acid.

The preparation of the anhydrous polymorph (Form X) of the D,L-tartrate salt of 5,8,14-triazatetracyclo[10.3.1.0$^{2,11}$.0$^{4,9}$]-hexadeca-2(11),3,5,7,9-pentaene involves the steps of dissolving 5,8,14-triazatetracyclo[10.3.1.0$^{2,11}$.0$^{4,9}$]-hexadeca-2(11),3,5,7,9-pentaene in a suitable solvent, preferably anhydrous ethanol, with about 1 to about 2.3 equivalents of D,L-tartaric acid, preferably 2.2 equivalents, at 20° C. to solvent reflux temperature for at least 2 hours, more preferably for at least 12 hours, most preferably at least 24 hours; collecting the crystals formed, washing the product with solvent and air drying it. The hydrate polymorph (Form Y) of the D,L-tartrate salt may be made in an analogous fashion but with the use of a solvent admixed with water, preferably an ethanol and water mixture, more preferably 20% aqueous ethanol. In addition, the meso-tartrate may be made in an analogous fashion to the D,L-tartrate.

Differential Scanning Calorimetry

Figure 9A:
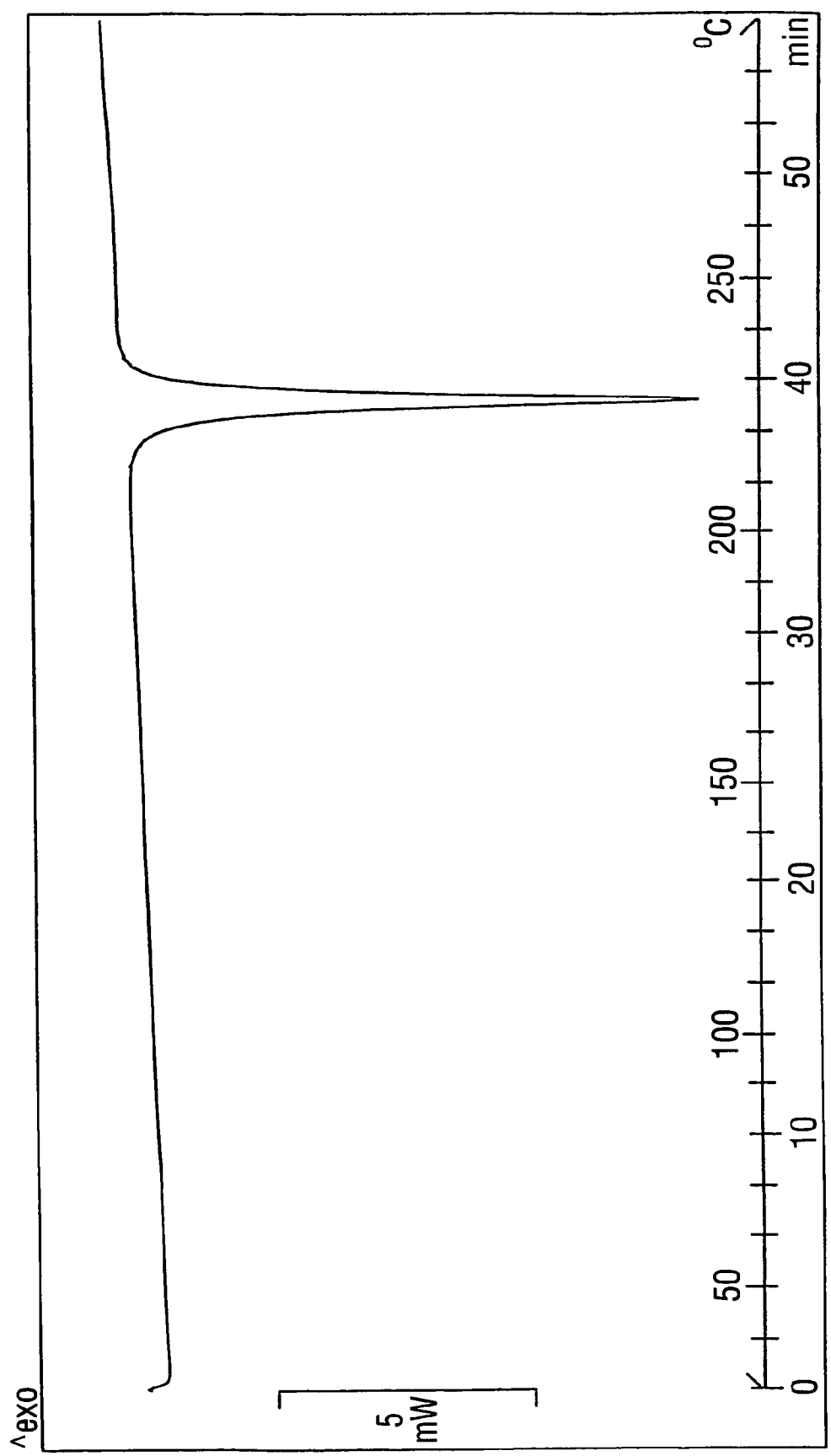
Figure 9B:
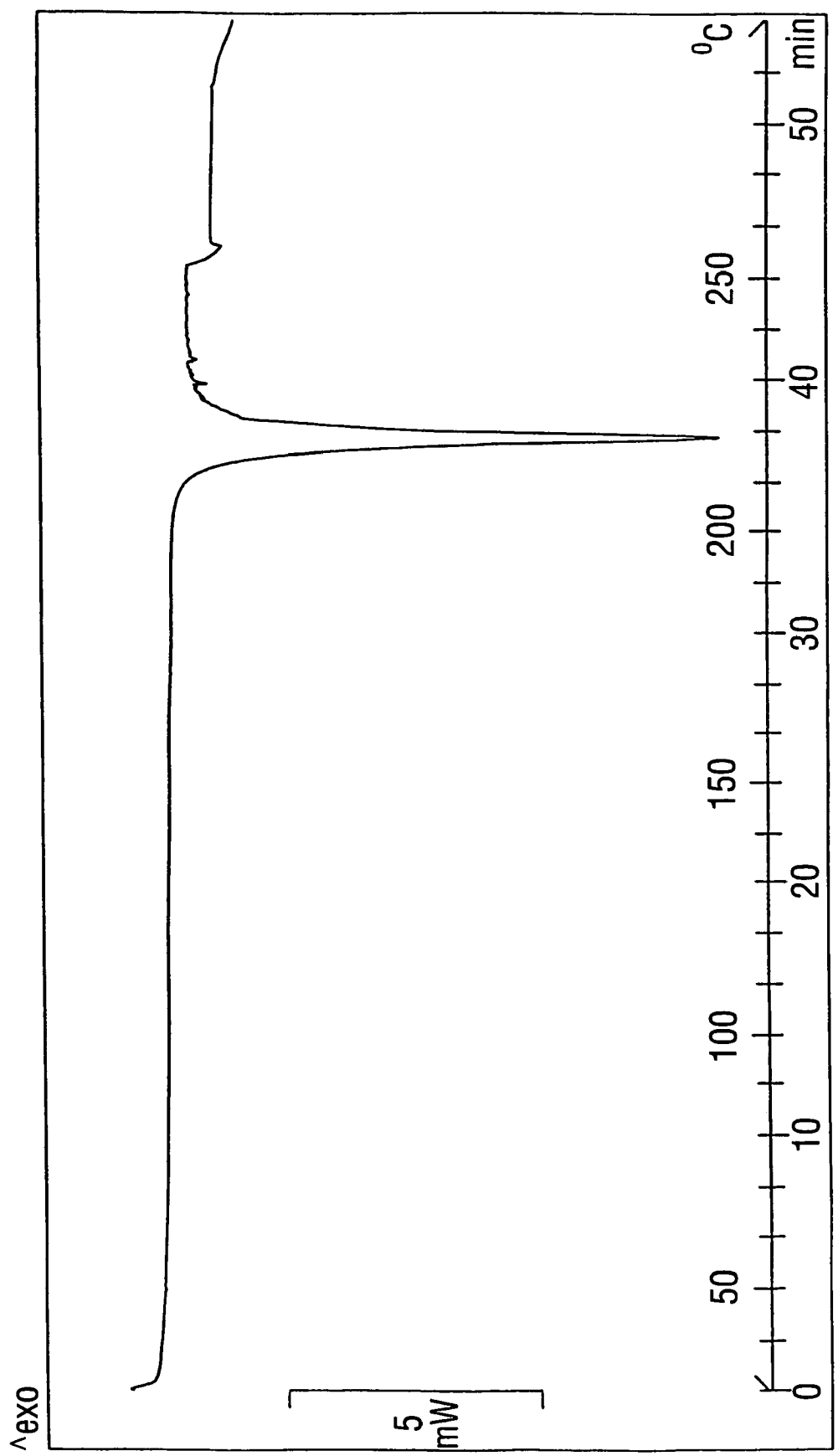

The solid state thermal behavior of Forms A, B and C of the L-tartrate salt of 5,8,14-triazatetra-cyclo[10.3.1.0$^{2,11}$.0$^{4,9}$]-hexadeca-2(11),3,5,7,9-pentaene were investigated by differential scanning calorimetry (DSC). The traces for Forms A, B and C are shown in FIGS. 9A, 9B and 9C, respectively. The DSC thermograms were obtained on a Meftler Toledo DSC 821® (STAR® System). Generally, samples between 1 and 10 mg were prepared in crimped aluminum pans with a small pinhole. The measurements were run at a heating rate of 5° C. per minute in the range of 30 to 300° C.

As seen in FIG. 9A, the L-tartrate salt Form A exhibits an onset of melt transition at 223° C. with a melting peak accompanied by decomposition at 225° C. measured at a rate of 5° C. per minute. As seen in FIG. 9B, the L-tartrate salt Form B exhibited an onset of melt transition at 215° C. with a melting peak accompanied by decomposition at 218° C. measured at a rate of 5° C. per minute. As seen in FIG. 9C, the L-tartrate salt hydrate Form C exhibits a solid-solid transition onset at 73° C. with a peak at 76° C. This solid-solid transition is believed to correspond to the loss of water from the crystal lattice. A melt transition onset is also observed at 220° C., with a peak at 223° C. accompanied by decomposition.

Figure 11A:
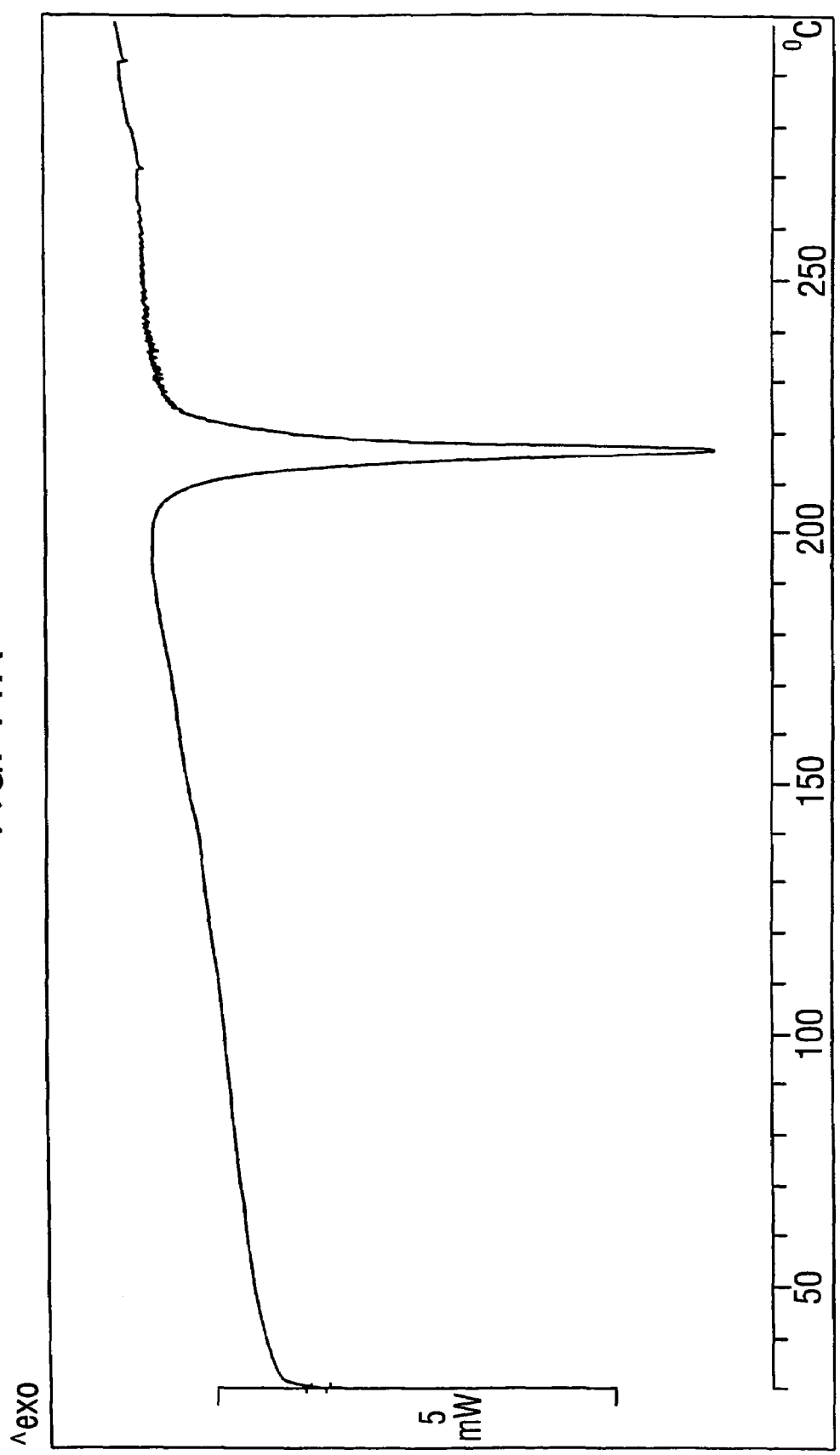
FIG. 11A and 11B are the differential scanning calorimetric traces for the D,L-tartrate salts Forms X and Y, respectively, of 5,8,14-triazatetra-cyclo[10.3.1.0$^{2,11}$.0$^{4,9}$]-hexadeca-2(11),3,5,7,9-pentaene.
Figure 11B:
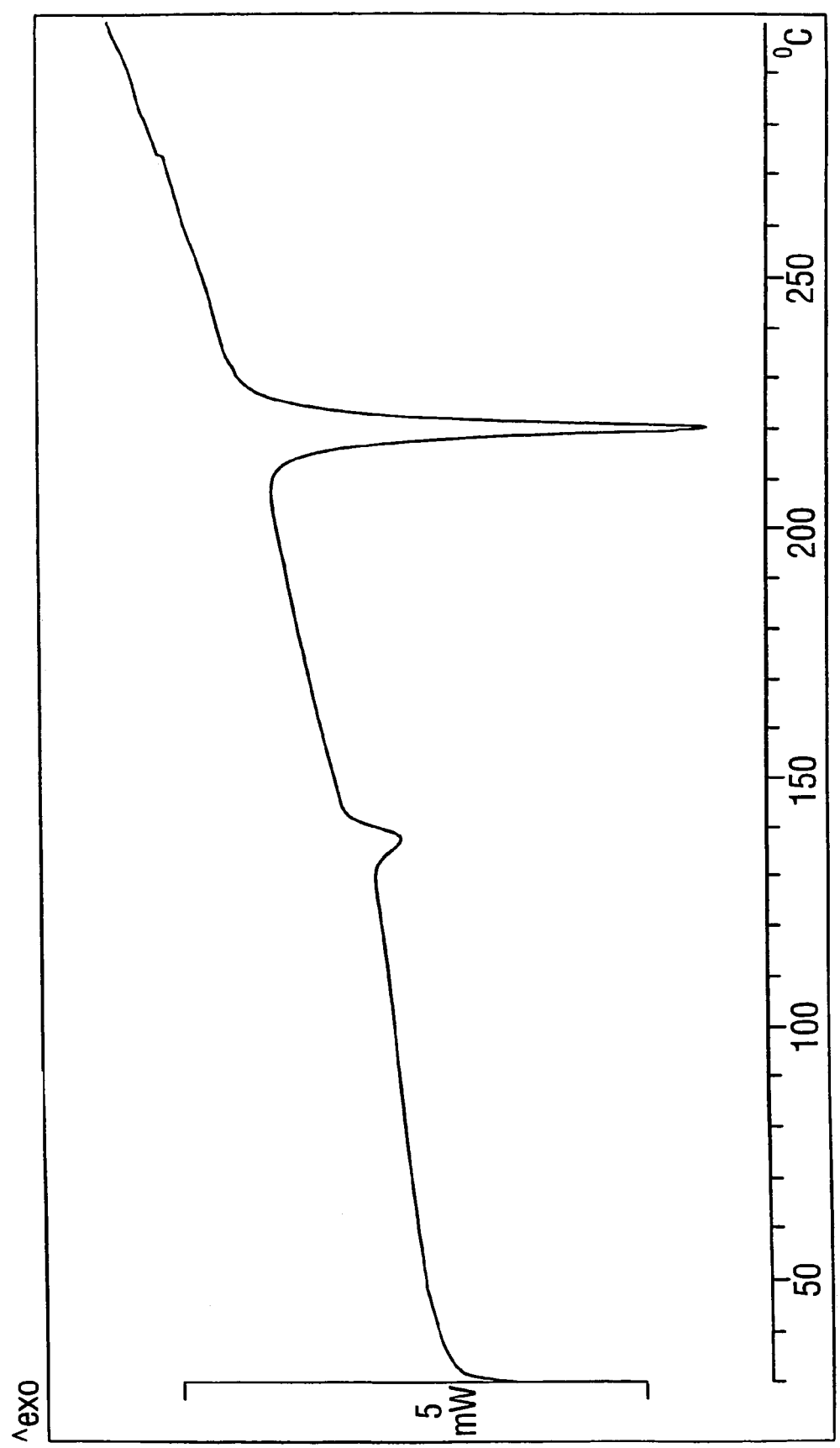

The solid state thermal behavior of Forms X and Y of the D,L-tartrate salt of 5,8,14-triazatetra-cyclo[10.3.1.0$^{2,11}$.0$^{4,9}$]-hexadeca-2(11),3,5,7,9-pentaene were also investigated by DSC. As seen in FIG. 11A, the D,L-tartrate salt Form X (anhydrous) exhibits an onset of melting transition at 212° C. In FIG. 11B, the differential scanning calorimetric trace for the D,L-tartrate salt Form Y indicates an exhibits a solid-solid transition onset at 131° C. with a peak at 137° C. This solid-solid transition is believed to correspond to or to be associated with the loss of water from the crystal lattice. A melt transition onset for Form Y is also observed at 217° C. and is accompanied by decomposition.

One of skill in the art will however note that in DSC measurements there is a certain degree of variability in actual measured onset and peak temperatures which is dependant on rate of heating, crystal shape and purity, and a number of measurement parameters.

Powder X-ray Diffraction Patterns

The powder x-ray diffraction patterns for both Forms A, B and C of the L-tartrate salt were collected using a Bruker D5000 diffractometer (Bruker AXS, Madison, Wis.) equipped with copper radiation (CuK$_a$), fixed slits (1.0, 1.0, 0.6 mm), and a Kevex solid state detector. Data was collected from 3.0 to 40.0 degrees in two theta (2θ) using a step size of 0.04 degrees and a step time of 1.0 seconds.

The x-ray powder diffraction pattern of the L-tartrate salt Form A was conducted with a copper anode with wavelength 1 at 1.54056 and wavelength 2 at 1.54439 (relative intensity: 0.500). The range for 2θ was between 3.0 to 40.0 degrees with a step size of 0.04 degrees, a step time of 1.00, a smoothing width of 0.300 and a threshold of 1.0.

Figure 1:
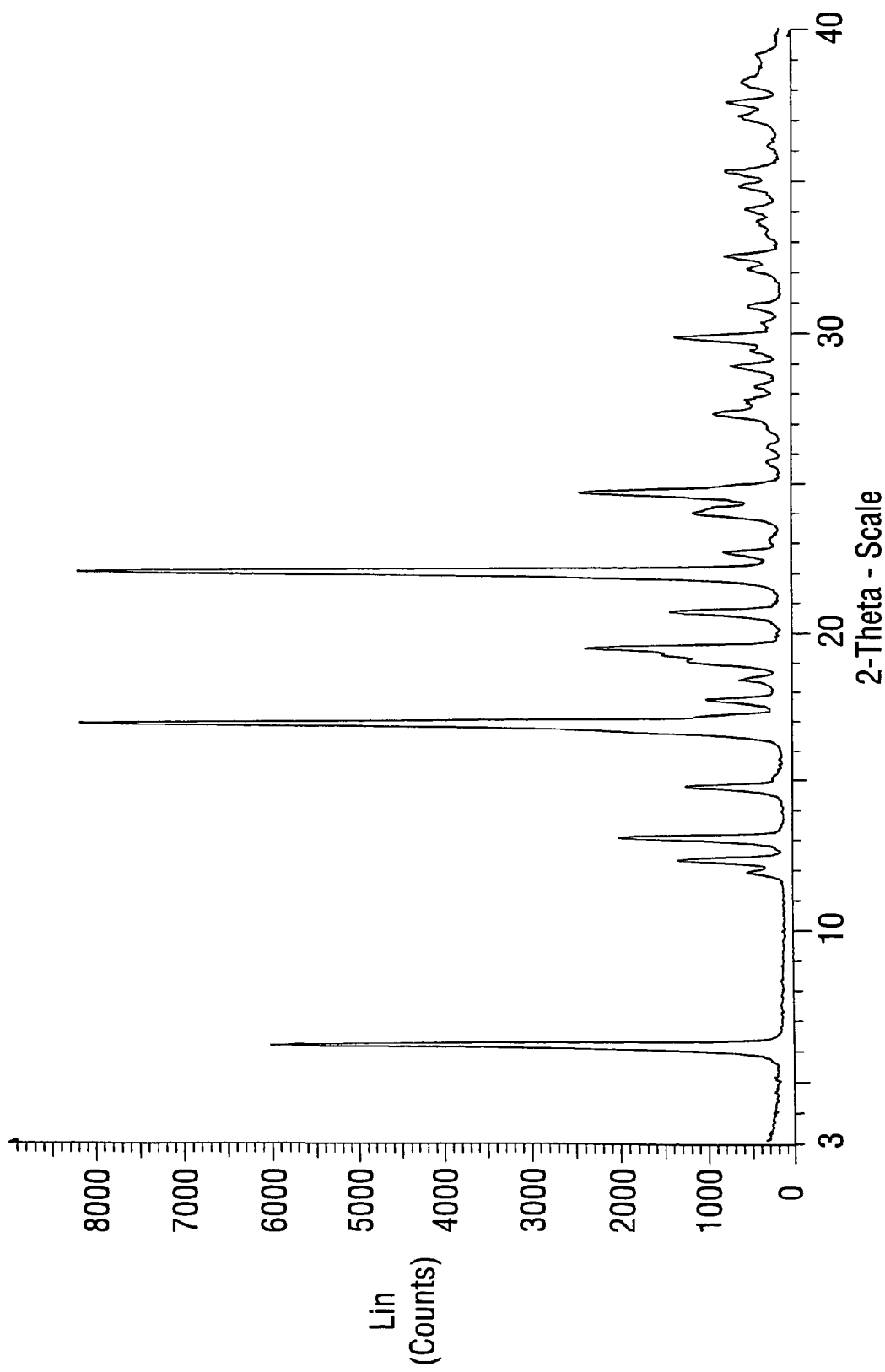
FIG. 1 is a powder X-ray diffraction of the anhydrous L-tartrate salt Form A of 5,8,14-triazatetracyclo[10.3.1.0$^{2,11}$.0$^{4,9}$]-hexadeca-2(11),3,5,7,9-pentaene (y axis is linear counts per second; X in degrees 2 theta).

The diffraction peaks at diffraction angles (2θ) in a measured powder X-ray diffraction analysis for the Form A are shown in Table I. The relative intensities, however, may change depending on the crystal size and morphology. The actual measured powder diffractogram is displayed in FIG. 1.

TABLE I

Powder X-ray Diffraction Pattern for L-Tartrate Form A with Intensities and Peak Locations of Diffraction Lines.

| Angle 2θ | d-value (Å) | I (rel.) |
|---|---|---|
| 6.1 | 14.5 | 73.3 |
| 11.8 | 7.5 | 6.1 |
| 12.2 | 7.2 | 15.8 |
| 13.0 | 6.8 | 23.9 |
| 14.7 | 6.0 | 14.6 |
| 16.8 | 5.3 | 99.5 |

TABLE I-continued

Powder X-ray Diffraction Pattern for L-Tartrate Form A with Intensities and Peak Locations of Diffraction Lines.

| Angle 2θ | d-value (Å) | I (rel.) |
|---|---|---|
| 17.6 | 5.0 | 11.7 |
| 18.3 | 4.8 | 7.0 |
| 19.0 | 4.7 | 14.4 |
| 19.4 | 4.6 | 28.4 |
| 20.6 | 4.3 | 16.8 |
| 21.9 | 4.1 | 100.0 |
| 22.6 | 3.9 | 9.1 |
| 23.9 | 3.7 | 13.4 |
| 24.6 | 3.6 | 29.2 |
| 27.2 | 3.3 | 10.5 |
| 27.7 | 3.2 | 6.1 |
| 28.8 | 3.1 | 8.0 |
| 29.4 | 3.0 | 5.3 |
| 29.8 | 3.0 | 15.9 |
| 30.8 | 2.9 | 5.6 |
| 32.0 | 2.8 | 5.8 |
| 32.5 | 2.8 | 8.9 |
| 34.0 | 2.6 | 6.0 |
| 34.8 | 2.6 | 6.9 |
| 35.2 | 2.5 | 8.8 |
| 37.0 | 2.4 | 6.9 |
| 37.5 | 2.4 | 8.6 |
| 38.2 | 2.4 | 6.5 |
| — | — | — |

Table II sets forth the 2θ, d-spacings and relative intensities representative of Form A. The numbers as listed are computer-generated.

TABLE II

Intensities and Peak Locations Representative of L-Tartrate Form A.

| Angle 2θ | d-value (Å) | I (rel.) |
|---|---|---|
| 6.1 | 14.5 | 73.3 |
| 12.2 | 7.2 | 15.8 |
| 13.0 | 6.8 | 23.9 |
| 14.7 | 6.0 | 14.6 |
| 16.8 | 5.3 | 99.5 |
| 19.4 | 4.6 | 28.4 |
| 21.9 | 4.1 | 100.0 |
| 24.6 | 3.6 | 29.2 |

Figure 2:
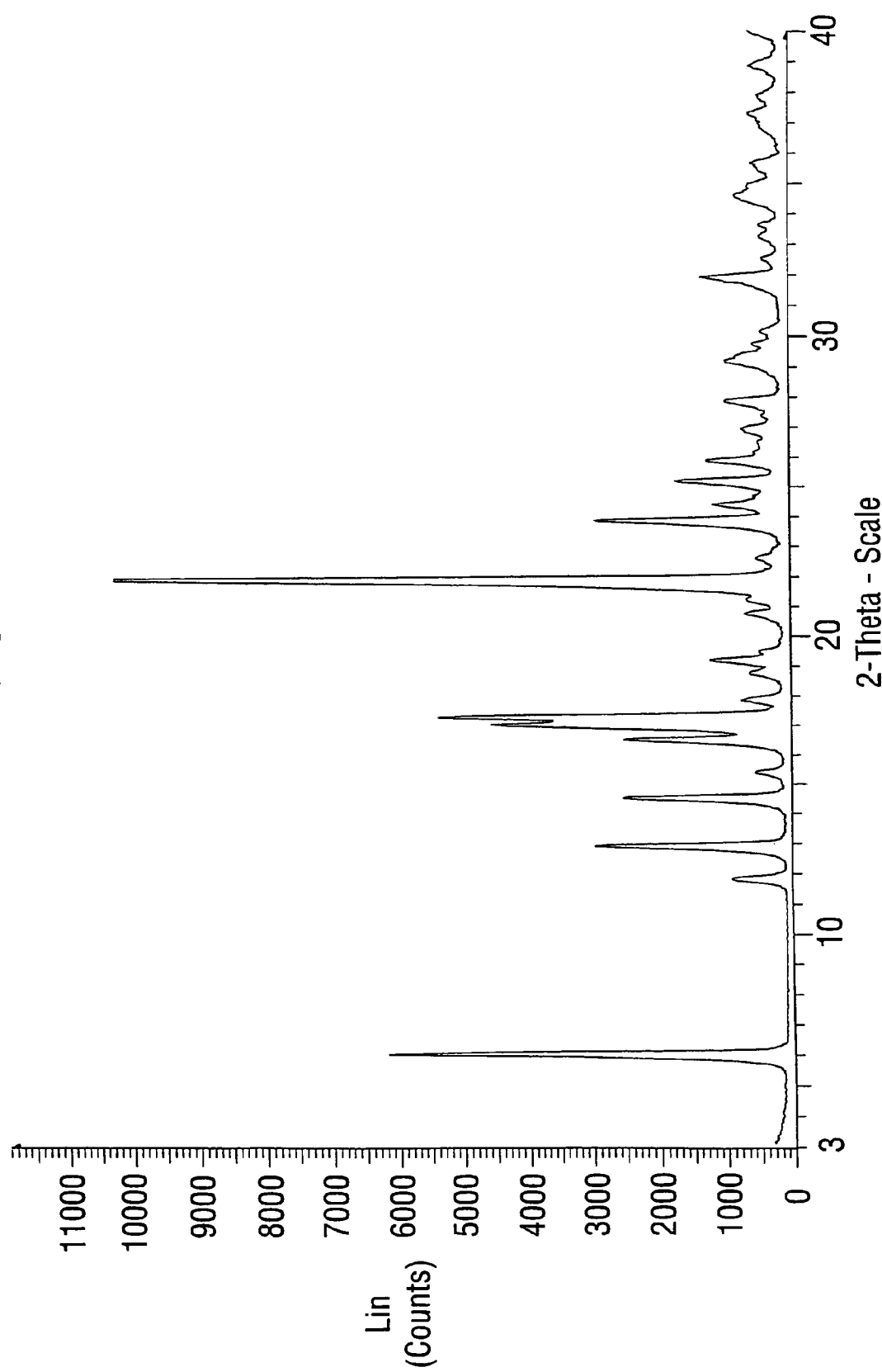
FIG. 2 is the powder X-ray diffraction of the anhydrous L-tartrate salt Form B of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

The x-ray powder diffraction pattern of the salt Form B was measured with the same equipment and under that same parameters used above for the measurement of Form A. The diffraction peaks at diffraction angles (2θ) in a measured powder X-ray diffraction analysis for the Form B are shown in Table III. Again, the relative intensities, however, may change depending on the crystal size and morphology. The actual measured powder diffractogram is displayed in FIG. 2.

TABLE III

Powder X-ray Diffraction Pattern for L-Tartrate Form B with Intensities and Peak Locations of Diffraction Lines.

| Angle 2θ | d-value (Å) | I (rel.) |
|---|---|---|
| 5.9 | 15.0 | 57.0 |
| 11.7 | 7.5 | 8.2 |
| 12.8 | 6.9 | 27.2 |

TABLE III-continued

Powder X-ray Diffraction Pattern for L-Tartrate Form B with Intensities and Peak Locations of Diffraction Lines.

| Angle 2θ | d-value (Å) | I (rel.) |
|---|---|---|
| 14.4 | 6.1 | 23.2 |
| 15.3 | 5.8 | 4.9 |
| 16.4 | 5.4 | 23.0 |
| 16.9 | 5.2 | 41.8 |
| 17.2 | 5.2 | 49.3 |
| 17.8 | 5.0 | 6.8 |
| 18.7 | 4.7 | 5.6 |
| 19.1 | 4.6 | 11.1 |
| 20.7 | 4.3 | 6.3 |
| 21.1 | 4.2 | 6.0 |
| 21.8 | 4.1 | 100.0 |
| 23.8 | 3.7 | 26.9 |
| 24.3 | 3.7 | 10.5 |
| 25.1 | 3.5 | 15.8 |
| 25.8 | 3.4 | 11.4 |
| 26.9 | 3.3 | 6.6 |
| 27.8 | 3.2 | 8.7 |
| 29.1 | 3.1 | 8.6 |
| 29.7 | 3.0 | 4.9 |
| 31.9 | 2.8 | 11.9 |
| 34.6 | 2.6 | 7.2 |
| 34.9 | 2.6 | 5.5 |
| 35.6 | 2.5 | 5.0 |
| 37.3 | 2.4 | 5.4 |
| 38.8 | 2.3 | 5.4 |
| — | — | — |

Table IV sets forth the 2θ, d-spacings, and relative intensities representative of Form B. The numbers as listed are computer-generated.

TABLE IV

Intensities and Peak Locations Representative of L-Tartrate Form B.

| Angle 2θ | d-value (Å) | I (rel.) |
|---|---|---|
| 5.9 | 15.0 | 57.0 |
| 12.8 | 6.9 | 27.2 |
| 14.4 | 6.1 | 23.2 |
| 15.3 | 5.8 | 4.9 |
| 16.9 | 5.2 | 41.8 |
| 17.2 | 5.2 | 49.3 |
| 21.8 | 4.1 | 100.0 |
| 23.8 | 3.7 | 26.9 |
| 25.1 | 3.5 | 15.8 |

Figure 3:
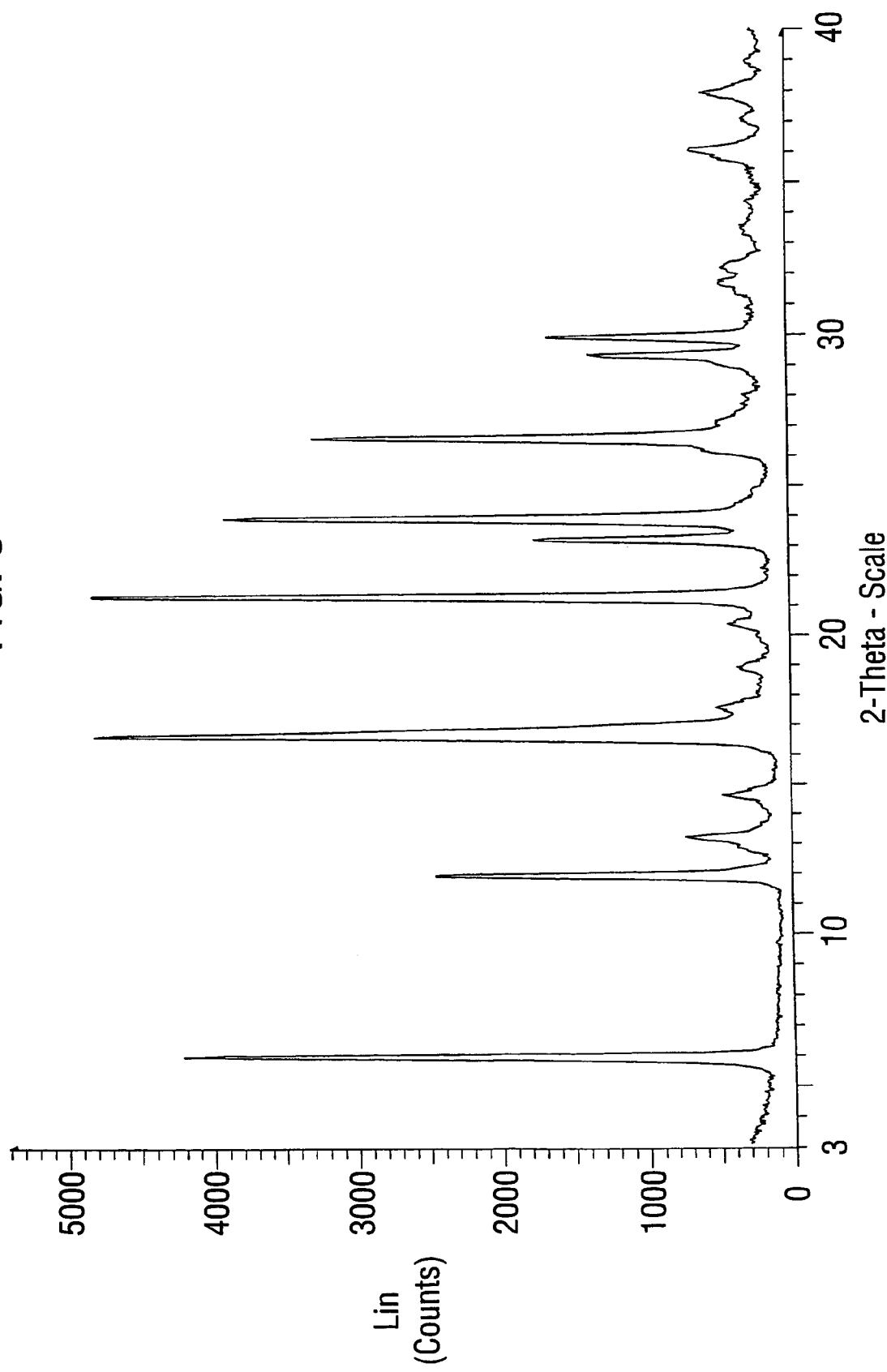
FIG. 3 is the powder X-ray diffraction of the L-tartrate salt hydrate Form C of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

The x-ray powder diffraction pattern of the salt Form C was measured with the same equipment and under that same parameters used above for the measurement of Form A. The diffraction peaks at diffraction angles (2θ) in a measured powder X-ray diffraction analysis for the Form C are shown in Table V. Again, the relative intensities, however, may change depending on the crystal size and morphology. The actual measured powder diffractogram is displayed in FIG. 3.

TABLE V

Powder X-ray Diffraction Pattern for L-Tartrate Form C with Intensities and Peak Locations of Diffraction Lines.

| Angle 2θ | d-value (Å) | I (rel.) |
|---|---|---|
| 5.9 | 15.1 | 85.5 |
| 11.8 | 7.5 | 49.4 |
| 13.1 | 6.8 | 14.4 |
| 14.5 | 6.1 | 9.2 |
| 16.5 | 5.4 | 97.4 |
| 17.5 | 5.1 | 10.0 |
| 18.8 | 4.7 | 7.0 |
| 20.3 | 4.4 | 8.2 |
| 21.2 | 4.2 | 100.0 |
| 23.1 | 3.8 | 35.0 |
| 23.8 | 3.7 | 78.5 |
| 26.1 | 3.4 | 11.6 |
| 26.5 | 3.4 | 65.8 |
| 27.0 | 3.3 | 9.6 |
| 27.9 | 3.2 | 5.8 |
| 28.9 | 3.1 | 9.5 |
| 29.3 | 3.0 | 27.3 |
| 29.9 | 3.0 | 33.0 |
| 31.3 | 2.9 | 6.7 |
| 31.6 | 2.8 | 9.0 |
| 32.1 | 2.8 | 8.7 |
| 33.5 | 2.7 | 5.9 |
| 35.8 | 2.5 | 10.0 |
| 36.0 | 2.5 | 13.0 |
| 37.0 | 2.4 | 5.7 |
| 37.9 | 2.4 | 11.5 |

Table VI sets forth the 2θ, d-spacings, and relative intensities representative of Form C. The numbers as listed are computer-generated.

TABLE VI

Intensities and Peak Locations Representative of L-Tartrate Form C.

| Angle 2θ | d-value (Å) | I (rel.) |
|---|---|---|
| 5.9 | 15.1 | 85.5 |
| 11.8 | 7.5 | 49.4 |
| 16.5 | 5.4 | 97.4 |
| 21.2 | 4.2 | 100.0 |
| 23.1 | 3.8 | 35.0 |
| 23.8 | 3.7 | 78.5 |
| 26.5 | 3.4 | 65.8 |

Figure 6:
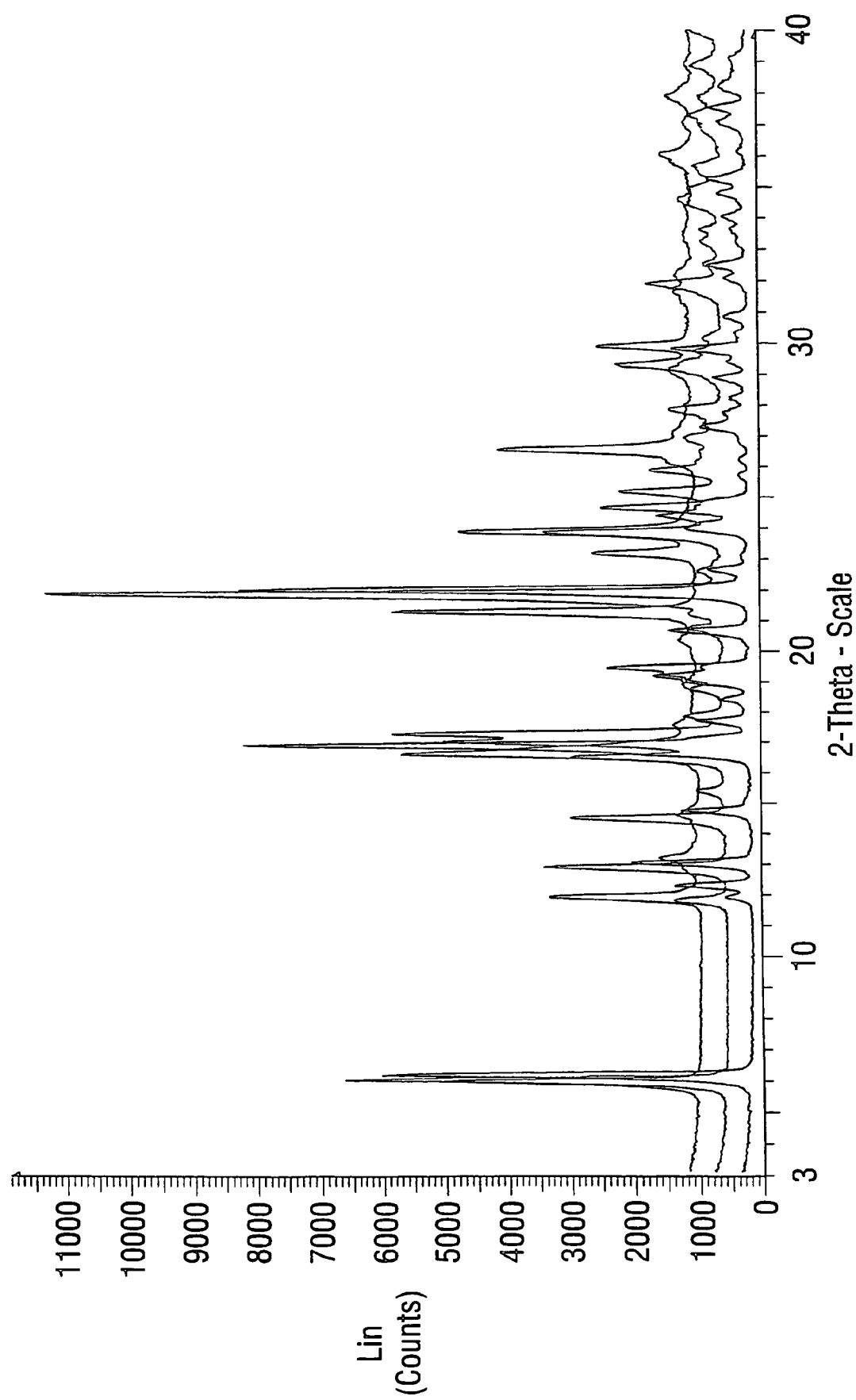
FIG. 6 is the overlay of the powder X-ray diffraction patterns of the Form A (lower trace), Form B (middle trace) and Form C (upper trace) L-tartrate salts of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

As shown in FIG. 6, the overlay of the observed x-ray powder diffraction patterns for L-tartrate salt Forms A, B and C shows some x-ray powder diffraction peak shifting and that each Form has a distinctive powder pattern fingerprint.

Figure 10A:
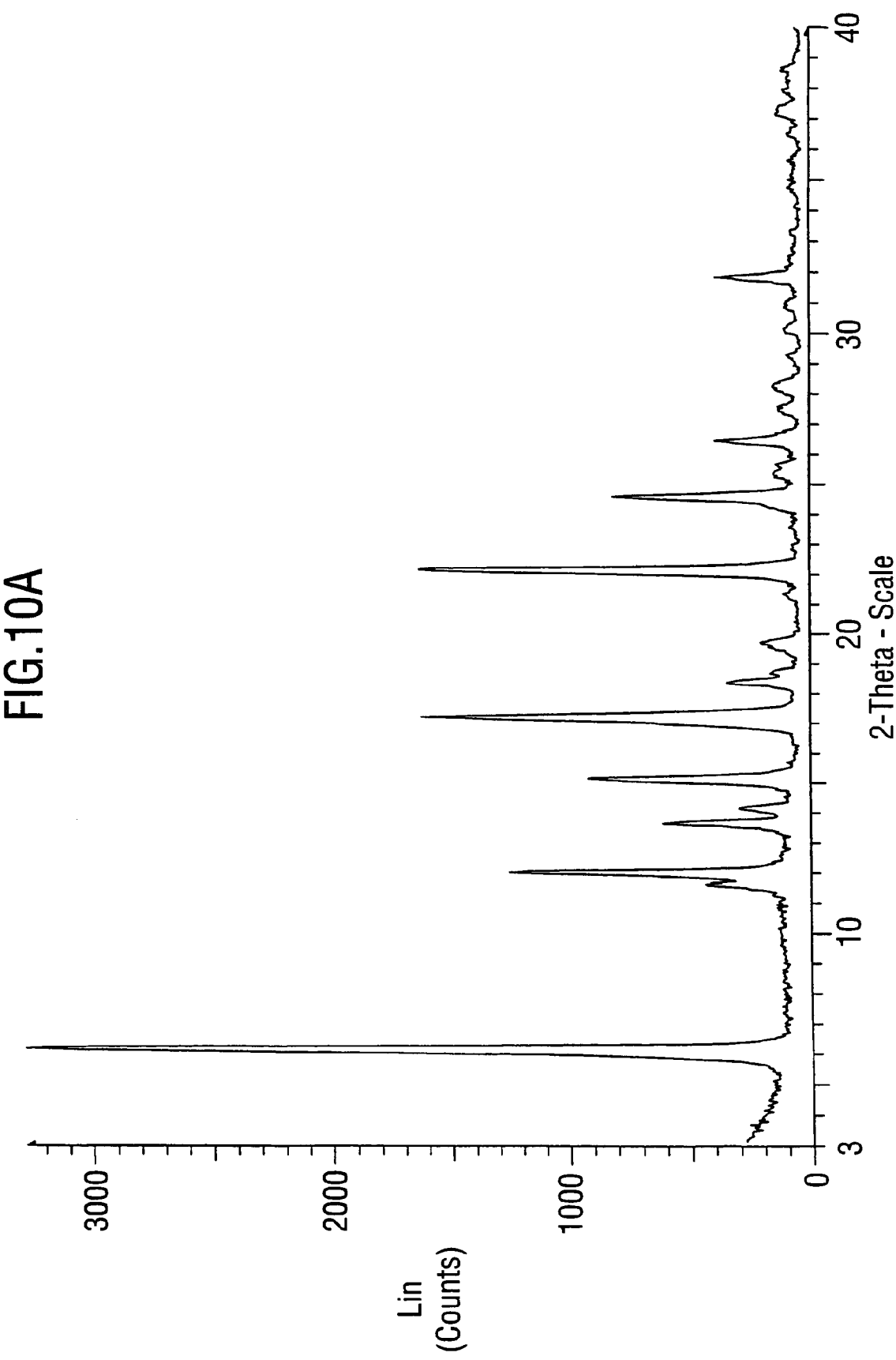
FIGS. 10A and 10B are the powder X-ray diffraction patterns of the D,L-tartrate salt Forms X and Y, respectively, of 5,8,14-triazatetracyclo[10.3.1.0$^{2,11}$.0$^{4,9}$]-hexadeca-2(11),3,5,7,9-pentaene (y axis is linear counts per second; X in degrees 2 theta).

The x-ray powder diffraction pattern of the D,L-tartrate salt Form X (anhydrous) was measured with the same equipment and under that same parameters used above for the measurement of Form A, L-tartrate salt. The diffraction peaks at diffraction angles (2θ) in a measured powder X-ray diffraction analysis for the Form X are shown in Table VII. Again, the relative intensities, however, may change depending on the crystal size and morphology. The actual measured powder diffractogram is displayed in FIG. 10A.

TABLE VII

Powder X-ray Diffraction Pattern for D,L-Tartrate Form X with Intensities and Peak Locations of Diffraction Lines.

| Angle 2θ | d-value (Å) | I (rel.) |
|---|---|---|
| 6.0 | 14.6 | 100.0 |
| 10.9 | 8.1 | 3.8 |
| 11.5 | 7.7 | 13.0 |
| 11.9 | 7.4 | 38.0 |
| 13.6 | 6.5 | 18.4 |
| 14.1 | 6.3 | 8.8 |
| 15.0 | 5.9 | 27.6 |
| 17.1 | 5.2 | 49.2 |
| 18.3 | 4.8 | 10.3 |
| 18.7 | 4.8 | 4.8 |
| 19.6 | 4.5 | 6.0 |
| 22.1 | 4.0 | 49.5 |
| 24.5 | 3.6 | 24.5 |
| 25.3 | 3.5 | 4.3 |
| 25.6 | 3.5 | 3.9 |
| 26.4 | 3.4 | 11.8 |
| 27.5 | 3.2 | 3.7 |
| 28.2 | 3.2 | 4.4 |
| 31.8 | 2.8 | 11.7 |
| 37.2 | 2.4 | 4.0 |
| 37.3 | 2.4 | 3.7 |

Table VIII sets forth the 2θ, d-spacings, and relative intensities representative of Form X. The numbers as listed are computer-generated.

TABLE VIII

Intensities and Peak Locations Representative of D,L-Tartrate Form X.

| Angle 2θ | d-value (Å) | I (rel.) |
|---|---|---|
| 6.0 | 14.6 | 100.0 |
| 11.9 | 7.4 | 38.0 |
| 15.0 | 5.9 | 27.6 |
| 17.1 | 5.2 | 49.2 |
| 22.1 | 4.0 | 49.5 |
| 24.5 | 3.6 | 24.5 |

Figure 10B:
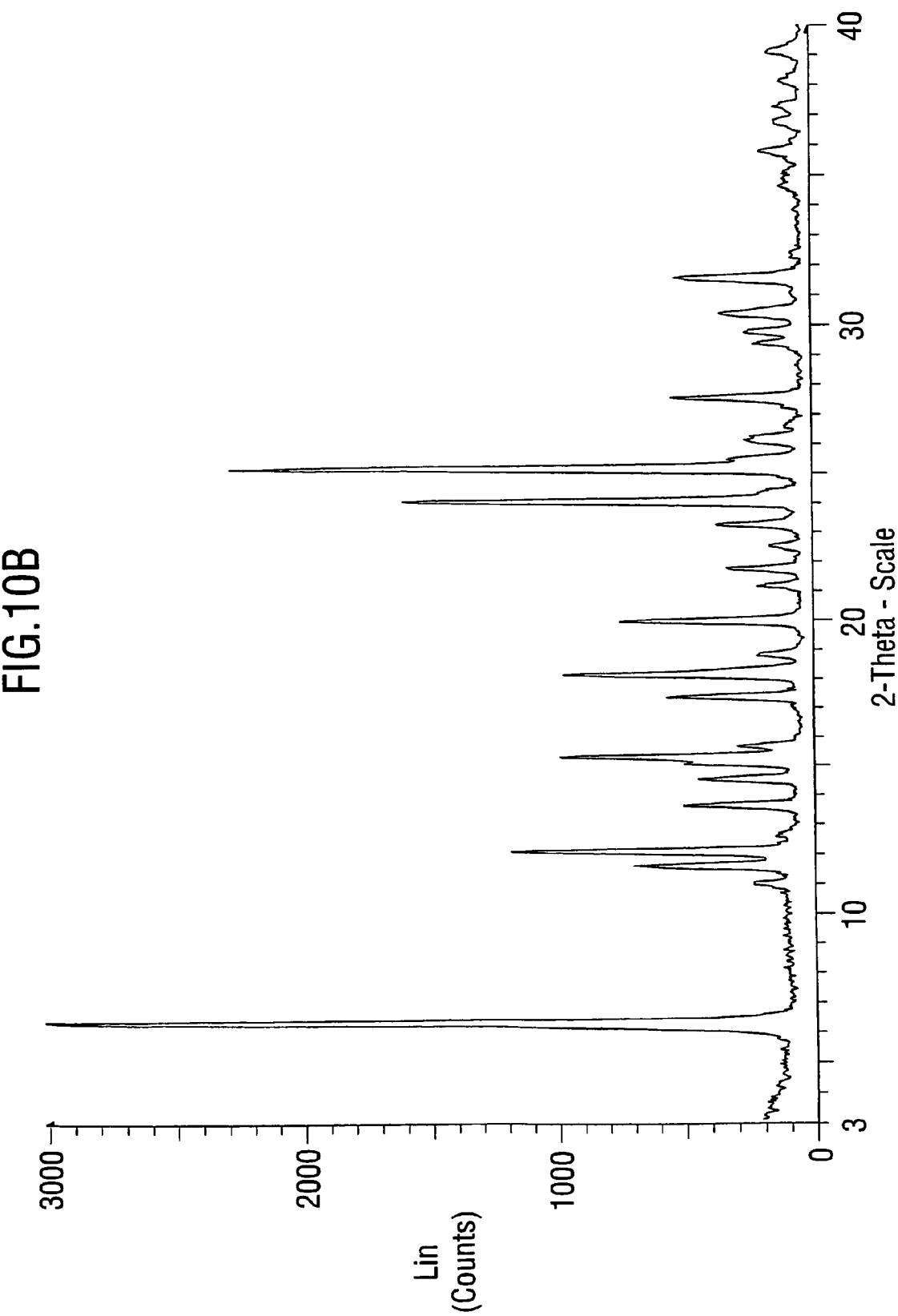

The x-ray powder diffraction pattern of the D,L-tartrate salt Form Y (hydrate) was measured with the same equipment and under that same parameters used above for the measurement of Form A, L-tartrate salt. The diffraction peaks at diffraction angles (2θ) in a measured powder X-ray diffraction analysis for the Form Y are shown in Table IX. Again, the relative intensities, however, may change depending on the crystal size and morphology. The actual measured powder diffractogram is displayed in FIG. 10B.

TABLE IX

Powder X-ray Diffraction Pattern for D,L-Tartrate Form Y with Intensities and Peak Locations of Diffraction Lines.

| Angle 2θ | d-value (Å) | I (rel.) |
|---|---|---|
| 4.1 | 21.4 | 5.2 |
| 6.2 | 14.2 | 100.0 |
| 10.9 | 8.1 | 7.8 |
| 11.5 | 7.7 | 23.1 |
| 12.0 | 7.4 | 39.1 |
| 12.5 | 7.1 | 4.6 |
| 13.5 | 6.5 | 16.6 |
| 14.4 | 6.1 | 14.7 |

TABLE IX-continued

Powder X-ray Diffraction Pattern for D,L-Tartrate Form Y with Intensities and Peak Locations of Diffraction Lines.

| Angle 2θ | d-value (Å) | I (rel.) |
|---|---|---|
| 15.0 | 5.9 | 16.4 |
| 15.2 | 5.8 | 32.7 |
| 15.6 | 5.7 | 9.6 |
| 17.3 | 5.1 | 18.6 |
| 18.1 | 4.9 | 32.2 |
| 18.7 | 4.7 | 7.1 |
| 19.9 | 4.5 | 24.7 |
| 21.1 | 4.2 | 7.0 |
| 21.7 | 4.1 | 11.0 |
| 22.5 | 4.0 | 5.4 |
| 23.2 | 3.8 | 12.2 |
| 24.0 | 3.7 | 52.7 |
| 25.1 | 3.5 | 75.1 |
| 25.5 | 3.5 | 10.3 |
| 26.1 | 3.4 | 8.5 |
| 27.5 | 3.2 | 17.9 |
| 29.3 | 3.0 | 7.4 |
| 29.7 | 3.0 | 8.4 |
| 30.3 | 2.9 | 11.7 |
| 31.5 | 2.8 | 17.4 |
| 35.8 | 2.5 | 6.4 |
| 36.7 | 2.4 | 4.5 |
| 37.3 | 2.4 | 4.6 |
| 39.1 | 2.3 | 5.4 |

Table X sets forth the 2θ, d-spacings and relative intensities of Form Y. The numbers as listed are computer-generated.

TABLE X

Intensities and Peak Locations Representative of D,L-Tartrate Form Y.

| Angle 2θ | d-value (Å) | I (rel.) |
|---|---|---|
| 6.2 | 14.2 | 100.0 |
| 12.0 | 7.4 | 39.1 |
| 15.2 | 5.8 | 32.7 |
| 18.1 | 4.9 | 32.2 |
| 24.0 | 3.7 | 52.7 |
| 25.1 | 3.5 | 75.1 |

Single Crystal X-ray Analysis

Single crystals for the L-tartrate salt Forms B and C were obtained and investigated by X-ray diffraction. For each form, a representative crystal was surveyed and a 1Å data set (maximum sin Θ/λ 0.5) was collected on a Siemens R4RA/v diffractometer. Atomic scattering factors were taken from the *International Tables for X-Ray Crystallography*, Vol. IV, pp. 55, 99 and 149 (Birmingham: Kynoch Press, 1974). Single crystal X-ray data were collected at room temperature. All crystallographic calculations were facilitated by the SHELXTL™ system (SHELXTL™ Reference Manual, Version 5.1, Bruker AXS, Madison, Wis. 1997). The pertinent crystal data collection and refinement are summarized in Table XI below for Form B and in Table XII below for Form C.

For both Forms, the trial structure was obtained by direct methods and was then refined routinely. A difference map revealed two waters of crystallization—one for each salt molecule. Hydrogen positions were calculated wherever possible. The hydrogens on nitrogen and oxygen were located by difference Fourier techniques. The hydrogen parameters were added to the structure factor calculations but were not refined. The shifts calculated in the final cycles of least squares refinement were all less than 0.1 of the corresponding standard deviations. For Form B, the final R-index was 3.25%. For Form C, the final R-index was 3.47%. A final difference Fourier revealed no missing or misplaced electron density. The refined structure was plotted using the SHELXTL plotting package and is shown in FIGS. 8A (Form B) and 8B (Form C). The absolute configuration was based on the use of L(+)-tartaric acid.

Table XIII sets forth the atomic coordinates ($\times 10^4$) and equivalent isotropic displacement parameters ($\text{Å}^2 \times 10^3$) for Form B. Table XIV lists the observed bond lengths [Å] and angles [°] for Form B. In Table XV, the anisotropic displacement parameters ($\text{Å}^2 \times 10^3$) for Form B are set forth to allow calculation of the anisotropic displacement factor exponent which has the form: $-2\pi^2[h^2 a^{*2} U_{11} + \ldots 2hka^*b^*U_{12}]$. Finally, in Table XVI, below, hydrogen coordinates ($\times 10^4$) and isotropic displacement parameters ($\text{Å}^2 \times 10^3$) for Form B are listed.

Table XVII sets forth the atomic coordinates ($\times 10^4$) and equivalent isotropic displacement parameters ($\text{Å}^2 \times 10^3$) for Form C. Table XVIII lists the observed bond lengths [Å] and angles [°] for Form C. In Table XIX, the anisotropic displacement parameters ($\text{Å}^2 \times 10^3$) for Form C are set forth to allow calculation of the anisotropic displacement factor exponent which has the form: $-2\pi^2[h^2 a^{*2} U_{11} + \ldots 2hka^*b^*U_{12}]$. Finally, in Table XX, below, hydrogen Coordinates ($\times 10^4$) and isotropic displacement parameters ($\text{Å}^2 \times 10^3$) for Form C are listed.

TABLE XI

Crystal Structure Data and Measurement Parameters: L-Tartrate Salt Form B

| Parameter | L-Tartrate Form B |
|---|---|
| Empirical formula | $C_{13}H_{14}N_3^+ C_4H_5O_6^-$ |
| Formula weight | 361.35 |
| Crystal System | Orthorhombic |
| Space Group | P2(1)2(1)2(1) |
| Crystal Size, mm³ | 0.01 × 0.08 × 0.10 |
| a | 7.0753(5) Å |
| b | 7.7846(5) Å |
| c | 29.870(2) Å |
| α | 90° |
| γ | 90° |
| β | 90° |
| Volume | 1645.21(19) Å³ |
| Density calc'd, ρ | 1.459 g/cm³ |
| Z | 4 |
| Temperature | 298(2) K |
| Wavelength | 1.54178 Å |
| Absorption coefficient | 0.944 mm⁻¹ |
| F(000) | 760 |
| Reflections collected | 3490 |
| Independent reflections | 1318 [R(int) = 0.0542] |
| Refinement method | Full-matrix least-squares on $F^2$ |
| Data/restraints/parameters | 1318/0/251 |
| Goodness-of-fit on $F^2$ | 0.856 |
| Final R indices [I > 2sigma(I)] | R1 = 0.0325, wR2 = 0.0638 |
| Absolute structure parameter | 0.0031(3) |
| Largest diff. peak and hole | 0.115 and −0.150 e. Å⁻³ |

TABLE XII

Crystal Structure Data and Measurement Parameters: L-Tartrate Salt Form C

| Parameter | L-Tartrate Hydrate Form C |
|---|---|
| Empirical formula | $C_{13}H_{14}N_3^+C_4H_5O_6^-\cdot H_2O$ |
| Formula weight | 379.37 |
| Crystal System | Monoclinic |
| Space Group | P2(1) |
| Crystal Size, mm$^3$ | 0.04 × 0.38 × 0.30 |
| X-ray Code | F611 |
| a | 7.5120 Å |
| b | 29.854 Å |
| c | 7.671 Å |
| α | 90° |
| γ | 90° |
| β | 90.40° |
| Volume | 1720.3 Å$^3$ |
| Density calc'd, ρ | 1.465 g/cm$^3$ |
| Z | 4 |
| Temperature | 298(2) K |
| Wavelength | 1.54178 Å |
| Absorption coefficient | 0.974 mm$^{-1}$ |
| F(000) | 800 |
| Reflections collected | 1983 |
| Independent reflections | 1817 [R(int) = 0.0224] |
| Refinement method | Full-matrix least-squares on F$^2$ |
| Data/restraints/parameters | 1817/0/528 |
| Goodness-of-fit on F$^2$ | 1.028 |
| Final R indices [I > 2sigma(I)] | R1 = 0.0347, wR2 = 0.0834 |
| Absolute structure parameter | 0.0(3) |
| Largest diff. peak and hole | 0.168 and −0.230 e. Å$^{-3}$ |

TABLE XIII

Atomic Coordinates (×10$^4$) And Equivalent Isotropic Displacement Parameters (Å$^2$ × 10$^3$) For Form B. U(eq) is defined as one third of the trace of the orthogonalized U$_{ij}$ tensor.

| | x | y | z | U(eq) |
|---|---|---|---|---|
| N(1) | 8211(8) | 10638(7) | 12233(1) | 61(1) |
| C(2) | 8968(8) | 9093(11) | 12235(2) | 72(2) |
| C(3) | 8093(11) | 7629(9) | 12047(2) | 75(2) |
| N(4) | 6431(8) | 7715(6) | 11853(1) | 64(1) |
| C(5) | 5624(9) | 9313(8) | 11834(2) | 50(1) |
| C(6) | 6502(8) | 10752(9) | 12025(2) | 49(1) |
| C(7) | 5676(8) | 12396(7) | 11985(1) | 48(1) |
| C(8) | 4007(8) | 12557(6) | 11762(2) | 41(1) |
| C(9) | 3107(7) | 11097(7) | 11572(1) | 42(1) |
| C(10) | 3890(8) | 9495(7) | 11605(1) | 49(1) |
| C(11) | 2865(7) | 14122(6) | 11634(1) | 44(1) |
| C(12) | 891(6) | 13347(5) | 11573(1) | 53(1) |
| C(13) | 1397(7) | 11686(6) | 11315(1) | 46(1) |
| C(14) | 3510(6) | 14823(6) | 11182(1) | 43(1) |
| N(15) | 3597(5) | 13405(5) | 10838(1) | 39(1) |
| C(16) | 1962(6) | 12183(5) | 10838(1) | 46(1) |
| C(20) | 7858(9) | 6393(6) | 10523(1) | 37(1) |
| O(21) | 9522(5) | 6116(4) | 10603(1) | 47(1) |
| O(22) | 6680(4) | 5324(4) | 10349(1) | 47(1) |
| C(23) | 7033(6) | 8162(5) | 10623(1) | 32(1) |
| O(24) | 5062(4) | 8318(4) | 10542(1) | 44(1) |
| C(25) | 8063(6) | 9486(5) | 10339(1) | 31(1) |
| O(26) | 7763(4) | 9176(4) | 9873(1) | 35(1) |
| C(27) | 7520(6) | 11321(6) | 10465(2) | 35(1) |
| O(28) | 7065(4) | 11655(6) | 10852(1) | 43(1) |
| O(29) | 7681(4) | 12417(4) | 10148(1) | 47(1) |

TABLE XIV

Bond lengths [Å] and angles [°] for L-Tartrate Form B.

Bond Lengths

| | | | |
|---|---|---|---|
| N(1)-C(2) | 1.316(6) | C(11)-C(12) | 1.532(6) |
| N(1)-C(6) | 1.362(6) | C(12)-C(13) | 1.547(6) |
| C(2)-C(3) | 1.413(7) | C(13)-C(16) | 1.531(5) |
| C(3)-N(4) | 1.314(7) | C(14)-N(15) | 1.510(5) |
| N(4)-C(5) | 1.370(6) | N(15)-C(16) | 1.498(5) |
| C(5)-C(10) | 1.411(6) | C(20)-O(21) | 1.221(5) |
| C(5)-C(6) | 1.403(7) | C(20)-O(22) | 1.288(5) |
| C(6)-C(7) | 1.412(6) | C(20)-C(23) | 1.525(6) |
| C(7)-C(8) | 1.361(6) | C(23)-O(24) | 1.420(5) |
| C(8)-C(9) | 1.421(6) | C(23)-C(25) | 1.521(5) |
| C(8)-C(11) | 1.511(6) | C(25)-O(26) | 1.428(5) |
| C(9)-C(10) | 1.368(6) | C(25)-C(27) | 1.526(6) |
| C(9)-C(13) | 1.504(6) | C(27)-O(28) | 1.227(5) |
| C(11)-C(14) | 1.526(5) | C(27)-O(29) | 1.281(5) |

Bond Angles

| | | | |
|---|---|---|---|
| C(2)-N(1)-C(6) | 115.0(5) | C(14)-C(11)-C(12) | 107.9(3) |
| N(1)-C(2)-C(3) | 123.9(5) | C(11)-C(12)-C(13) | 100.2(3) |
| N(4)-C(3)-C(2) | 121.8(5) | C(9)-C(13)-C(16) | 110.0(4) |
| C(3)-N(4)-C(5) | 116.0(5) | C(9)-C(13)-C(12) | 100.8(4) |
| N(4)-C(5)-C(10) | 118.3(6) | C(16)-C(13)-C(12) | 108.2(4) |
| N(4)-C(5)-C(6) | 121.5(6) | N(15)-C(14)-C(11) | 110.6(4) |
| C(10)-C(5)-C(6) | 120.2(6) | C(16)-N(15)-C(14) | 115.7(3) |
| N(1)-C(6)-C(5) | 121.8(6) | N(15)-C(16)-C(13) | 111.2(3) |
| N(1)-C(6)-C(7) | 117.8(6) | O(21)-C(20)-O(22) | 126.1(5) |
| C(5)-C(6)-C(7) | 120.3(5) | O(21)-C(20)-C(23) | 119.4(5) |
| C(8)-C(7)-C(6) | 119.0(5) | O(22)-C(20)-C(23) | 114.5(5) |
| C(7)-C(8)-C(9) | 120.7(5) | O(24)-C(23)-C(25) | 108.5(3) |
| C(7)-C(8)-C(11) | 131.5(5) | O(24)-C(23)-C(20) | 114.8(4) |
| C(9)-C(8)-C(11) | 107.4(4) | C(25)-C(23)-C(20) | 108.6(3) |
| C(10)-C(9)-C(8) | 121.2(5) | O(26)-C(25)-C(23) | 111.0(3) |
| C(10)-C(9)-C(13) | 129.8(5) | O(26)-C(25)-C(27) | 111.2(3) |
| C(8)-C(9)-C(13) | 108.7(5) | C(23)-C(25)-C(27) | 112.0(4) |
| C(9)-C(10)-C(5) | 118.6(5) | O(28)-C(27)-O(29) | 125.4(4) |
| C(8)-C(11)-C(14) | 110.7(4) | O(28)-C(27)-C(25) | 119.8(4) |
| C(8)-C(11)-C(12) | 101.6(4) | O(29)-C(27)-C(25) | 114.7(4) |

TABLE XV

Anisotropic Displacement Parameters (Å$^2$ × 10$^3$) For Form B. (The Anisotropic displacement factor exponent takes the form: $-2\pi^2[h^2 a^{*2}U_{11} + \ldots + 2hka^*b^*U_{12}]$).

| | U$_{11}$ | U$_{22}$ | U$_{33}$ | U$_{23}$ | U$_{13}$ | U$_{12}$ |
|---|---|---|---|---|---|---|
| N(1) | 63(4) | 70(4) | 50(3) | 12(2) | −2(3) | 8(3) |
| C(2) | 54(4) | 114(6) | 49(4) | 20(4) | −3(3) | 8(5) |
| C(3) | 79(5) | 78(5) | 66(4) | 14(4) | −6(4) | 30(5) |
| N(4) | 78(4) | 54(4) | 60(3) | 8(3) | −9(3) | 13(3) |
| C(5) | 65(4) | 45(4) | 39(3) | 5(3) | −3(3) | 6(4) |
| C(6) | 41(4) | 69(5) | 36(3) | 8(3) | −9(3) | 1(4) |
| C(7) | 51(4) | 56(5) | 38(3) | 3(3) | −2(3) | −5(4) |
| C(8) | 45(4) | 41(4) | 38(3) | 4(3) | 1(3) | −3(4) |
| C(9) | 46(4) | 40(4) | 40(3) | 12(3) | 9(3) | −4(4) |
| C(10) | 54(4) | 52(5) | 41(3) | 8(3) | −5(3) | −14(4) |
| C(11) | 49(3) | 43(3) | 38(3) | −1(3) | 1(3) | −1(3) |
| C(12) | 45(4) | 63(4) | 50(3) | 6(3) | 7(3) | 3(3) |
| C(13) | 42(3) | 49(3) | 48(3) | 11(3) | −3(3) | −4(3) |
| C(14) | 43(3) | 39(3) | 46(3) | −3(3) | 2(3) | −1(3) |
| N(15) | 35(3) | 41(3) | 40(2) | 7(2) | 3(2) | −2(2) |
| C(16) | 42(3) | 51(3) | 44(3) | 6(3) | −4(3) | −2(3) |
| C(20) | 48(4) | 30(4) | 33(3) | 9(3) | 10(3) | −6(4) |
| O(21) | 30(2) | 41(2) | 68(2) | 3(2) | −5(2) | 7(2) |
| O(22) | 44(2) | 22(2) | 73(2) | −5(2) | −2(2) | 2(2) |
| C(23) | 26(3) | 28(3) | 42(3) | 0(2) | 7(2) | 0(3) |
| O(24) | 33(2) | 33(2) | 68(2) | −10(2) | 4(2) | 1(2) |
| C(25) | 35(3) | 25(3) | 32(3) | −7(2) | −1(2) | 4(3) |
| O(26) | 35(2) | 32(2) | 38(2) | −5(1) | 3(2) | −1(2) |
| C(27) | 22(3) | 40(4) | 42(4) | −7(3) | −8(3) | 1(3) |
| O(28) | 53(2) | 36(2) | 41(2) | −7(2) | 2(2) | 2(2) |
| O(29) | 74(2) | 27(2) | 41(2) | 5(2) | 7(2) | 4(2) |

TABLE XVI

Hydrogen Coordinates (×10⁴) And Isotropic Displacement Parameters ($Å^2 \times 10^3$) For Form B.

| | x | y | z | U(eq) |
|---|---|---|---|---|
| H(2A) | 10149 | 8958 | 12367 | 80 |
| H(3A) | 8710 | 6576 | 12062 | 80 |
| H(7A) | 6264 | 13354 | 12108 | 80 |
| H(10A) | 3292 | 8546 | 11480 | 80 |
| H(11A) | 2887 | 15004 | 11868 | 80 |
| H(12A) | 76 | 14092 | 11398 | 80 |
| H(12B) | 295 | 13097 | 11858 | 80 |
| H(13A) | 372 | 10840 | 11321 | 80 |
| H(14A) | 2636 | 15704 | 11082 | 80 |
| H(14B) | 4748 | 15344 | 11213 | 80 |
| H(15A) | 3600(70) | 14000(60) | 10578(14) | 80 |
| H(15B) | 4860(70) | 12850(60) | 10867(14) | 80 |
| H(16A) | 2302 | 11156 | 10672 | 80 |
| H(16B) | 894 | 12713 | 10688 | 80 |
| H(23A) | 7270 | 8427 | 10939 | 80 |
| H(24A) | 4680(70) | 7400(60) | 10401(15) | 80 |
| H(25A) | 9419 | 9355 | 10397 | 80 |
| H(26A) | 6710(70) | 9120(70) | 9841(17) | 80 |
| H(29A) | 7180(60) | 13930(80) | 10298(14) | 80 |

TABLE XVII

Atomic Coordinates (×10⁴) And Equivalent Isotropic Displacement Parameters ($Å^2 \times 10^3$) For Form C. U(eq) is defined as one third of the trace of the orthogonalized $U_{ij}$ tensor.

| | x | y | z | U(eq) |
|---|---|---|---|---|
| N(1) | −159(7) | 10186(3) | −1642(7) | 45(1) |
| C(2) | −239(10) | 10333(3) | −58(10) | 52(2) |
| C(3) | 1241(10) | 10446(3) | 959(9) | 50(2) |
| N(4) | 2878(7) | 10415(3) | 368(6) | 42(1) |
| C(5) | 3033(8) | 10257(3) | −1310(8) | 33(2) |
| C(6) | 1520(7) | 10141(3) | −2302(8) | 30(2) |
| C(7) | 1723(7) | 9967 | −4007(7) | 32(2) |
| C(8) | 3381(7) | 9902(3) | −4622(7) | 25(1) |
| C(9) | 4905(7) | 10018(3) | −3648(7) | 25(1) |
| C(10) | 4759(8) | 10194(3) | −2016(8) | 36(2) |
| C(11) | 6537(7) | 9881(3) | −4655(7) | 31(2) |
| C(12) | 7003(7) | 9395(3) | −4191(7) | 33(2) |
| N(13) | 5380(6) | 9102(3) | −4292(6) | 27(1) |
| C(14) | 4292(7) | 9171(3) | −5922(7) | 29(1) |
| C(15) | 4011(7) | 9668(3) | −6277(7) | 28(1) |
| C(16) | 5826(8) | 9887(3) | −6550(8) | 41(2) |
| C(1X) | 1541(7) | 7444(3) | −5634(8) | 23(1) |
| O(2X) | 1182(4) | 7444(2) | −7182(5) | 36(1) |
| O(3X) | 361(5) | 7474(2) | −4418(5) | 38(1) |
| C(4X) | 3457(6) | 7425(3) | −4997(7) | 24(1) |
| O(5X) | 3649(5) | 7280(2) | −3247(5) | 32(1) |
| C(6X) | 4282(7) | 7881(3) | −5336(7) | 25(1) |
| O(7X) | 3348(4) | 8230(2) | −4482(5) | 28(1) |
| C(8X) | 6296(7) | 7900(3) | −4948(7) | 22(1) |
| O(9X) | 7172(5) | 7560(2) | −5428(5) | 37(1) |
| O(10X) | 6935(5) | 8241(2) | −4266(5) | 35(1) |
| O(1W) | 3226(6) | 7996(2) | −924(5) | 37(1) |
| N(51) | 3493(6) | 6295(3) | 3311(7) | 43(1) |
| C(52) | 3598(9) | 6141(3) | 4922(9) | 47(2) |
| C(53) | 2144(9) | 6031(3) | 5890(8) | 45(2) |
| N(54) | 494(7) | 6065(3) | 5313(7) | 43(1) |
| C(55) | 289(8) | 6228(3) | 3651(7) | 30(1) |
| C(56) | 1799(7) | 6340(3) | 2642(8) | 30(2) |
| C(57) | 1574(8) | 6528(2) | 950(8) | 32(2) |
| C(58) | −95(8) | 6593(3) | 320(7) | 27(1) |
| C(59) | −1609(7) | 6472(2) | 1339(7) | 25(1) |
| C(60) | −1436(7) | 6295(3) | 2965(9) | 35(2) |
| C(61) | −3249(8) | 6621(3) | 334(8) | 32(2) |
| C(62) | −3717(7) | 7097(3) | 850(7) | 33(2) |
| N(63) | −2088(6) | 7392(3) | 720(6) | 26(1) |
| C(64) | −1014(7) | 7329(3) | −916(6) | 29(1) |
| C(65) | −765(7) | 6828(3) | −1308(7) | 30(1) |
| C(66) | −2599(8) | 6612(3) | −1564(7) | 36(2) |
| C(1Y) | −2999(7) | 8598(3) | 27(7) | 26(1) |
| O(2Y) | −3633(5) | 8257(2) | 745(5) | 35(1) |
| O(3Y) | −3884(5) | 8934(2) | −462(5) | 34(1) |
| C(4Y) | −986(6) | 8611(3) | −356(7) | 20(1) |
| O(5Y) | −53(4) | 8261(2) | 523(5) | 28(1) |
| C(6Y) | −163(7) | 9070(3) | −16(7) | 23(1) |
| O(7Y) | −328(5) | 9219(2) | 1725(5) | 33(1) |
| C(8Y) | 1746(7) | 9048(3) | −658(8) | 24(1) |
| O(9Y) | 2954(5) | 9023(2) | 572(5) | 36(1) |
| O(10Y) | 2085(5) | 9039(2) | −2209(5) | 37(1) |
| O(2W) | 54(6) | 8500(2) | 4066(5) | 39(1) |

TABLE XVIII

Bond lengths [Å] and angles [°] for L-Tartrate Form C.

Bond Lengths (Form C)

| | | | |
|---|---|---|---|
| N(1)-C(2) | 1.294(8) | N(51)-C(52) | 1.320(8) |
| N(1)-C(6) | 1.369(7) | N(51)-C(56) | 1.375(7) |
| C(2)-C(3) | 1.396(10) | C(52)-C(53) | 1.365(9) |
| C(3)-N(4) | 1.316(8) | C(53)-N(54) | 1.317(8) |
| N(4)-C(5) | 1.377(8) | N(54)-C(55) | 1.373(8) |
| C(5)-C(6) | 1.407(8) | C(55)-C(60) | 1.410(8) |
| C(5)-C(10) | 1.421(9) | C(55)-C(56) | 1.417(8) |
| C(6)-C(7) | 1.417(8) | C(56)-C(57) | 1.424(8) |
| C(7)-C(8) | 1.349(8) | C(57)-C(58) | 1.355(8) |
| C(8)-C(9) | 1.407(8) | C(58)-C(59) | 1.431(8) |
| C(8)-C(15) | 1.526(8) | C(58)-C(65) | 1.514(8) |
| C(9)-C(10) | 1.362(8) | C(59)-C(60) | 1.360(8) |
| C(9)-C(11) | 1.511(8) | C(59)-C(61) | 1.515(8) |
| C(11)-C(12) | 1.534(8) | C(61)-C(62) | 1.518(9) |
| C(11)-C(16) | 1.545(8) | C(61)-C(66) | 1.539(8) |

TABLE XVIII-continued

Bond lengths [Å] and angles [°] for L-Tartrate Form C.

| | | | | |
|---|---|---|---|---|
| C(12)-N(13) | 1.501(7) | C(62)-N(63) | 1.511(7) |
| N(13)-C(14) | 1.504(6) | N(63)-C(64) | 1.508(6) |
| C(14)-C(15) | 1.525(8) | C(64)-C(65) | 1.537(8) |
| C(15)-C(16) | 1.528(8) | C(65)-C(66) | 1.533(8) |
| C(1X)-O(2X) | 1.216(6) | C(1Y)-O(3Y) | 1.259(7) |
| C(1X)-O(3X) | 1.295(6) | C(1Y)-O(2Y) | 1.254(7) |
| C(1X)-C(4X) | 1.518(7) | C(1Y)-C(4Y) | 1.543(8) |
| C(4X)-O(5X) | 1.417(6) | C(4Y)-O(5Y) | 1.424(6) |
| C(4X)-C(6X) | 1.517(8) | C(4Y)-C(6Y) | 1.526(8) |
| C(6X)-O(7X) | 1.419(7) | C(6Y)-O(7Y) | 1.413(7) |
| C(6X)-C(8X) | 1.541(7) | C(6Y)-C(8Y) | 1.521(8) |
| C(8X)-O(10X) | 1.240(7) | C(8Y)-O(10Y) | 1.219(6) |
| C(8X)-O(9X) | 1.267(7) | C(8Y)-O(9Y) | 1.306(7) |

Bond Angles (Form C)

| | | | | |
|---|---|---|---|---|
| C(2)-N(1)-C(6) | 115.5(6) | C(52)-N(51)-C(56) | 115.6(5) |
| N(1)-C(2)-C(3) | 124.4(7) | N(51)-C(52)-C(53) | 123.4(6) |
| N(4)-C(3)-C(2) | 122.2(6) | N(54)-C(53)-C(52) | 123.6(6) |
| C(3)-N(4)-C(5) | 115.6(6) | C(53)-N(54)-C(55) | 116.0(5) |
| N(4)-C(5)-C(6) | 121.1(6) | N(54)-C(55)-C(60) | 119.6(5) |
| N(4)-C(5)-C(10) | 119.0(5) | N(54)-C(55)-C(56) | 120.4(5) |
| C(6)-C(5)-C(10) | 119.8(6) | C(60)-C(55)-C(56) | 120.0(5) |
| N(1)-C(6)-C(5) | 121.3(6) | N(51)-C(56)-C(55) | 121.0(6) |
| N(1)-C(6)-C(7) | 118.9(5) | N(51)-C(56)-C(57) | 118.8(5) |
| C(5)-C(6)-C(7) | 119.9(5) | C(55)-C(56)-C(57) | 120.1(5) |
| C(8)-C(7)-C(6) | 118.8(5) | C(58)-C(57)-C(56) | 119.0(5) |
| C(7)-C(8)-C(9) | 121.9(5) | C(57)-C(58)-C(59) | 120.4(5) |
| C(7)-C(8)-C(15) | 130.5(5) | C(57)-C(58)-C(65) | 131.4(5) |
| C(9)-C(8)-C(15) | 107.4(5) | C(59)-C(58)-C(65) | 107.9(5) |
| C(10)-C(9)-C(8) | 120.9(5) | C(60)-C(59)-C(58) | 121.9(5) |
| C(10)-C(9)-C(11) | 130.2(5) | C(60)-C(59)-C(61) | 130.8(5) |
| C(8)-C(9)-C(11) | 108.7(5) | C(58)-C(59)-C(61) | 107.1(5) |
| C(9)-C(10)-C(5) | 118.7(5) | C(59)-C(60)-C(55) | 118.7(5) |
| C(9)-C(11)-C(12) | 108.9(5) | C(59)-C(61)-C(62) | 109.2(5) |
| C(9)-C(11)-C(16) | 101.6(5) | C(59)-C(61)-C(66) | 102.4(5) |
| C(12)-C(11)-C(16) | 107.9(5) | C(62)-C(61)-C(66) | 109.8(5) |
| N(13)-C(12)-C(11) | 110.8(5) | N(63)-C(62)-C(61) | 109.8(5) |
| C(14)-N(13)-C(12) | 113.6(4) | C(64)-N(63)-C(62) | 114.9(4) |

Bond Angles (Form C)

| | | | | |
|---|---|---|---|---|
| N(13)-C(14)-C(15) | 110.8(4) | N(63)-C(64)-C(65) | 110.6(4) |
| C(16)-C(15)-C(14) | 108.6(5) | C(58)-C(65)-C(66) | 101.8(4) |
| C(16)-C(15)-C(8) | 101.6(4) | C(58)-C(65)-C(64) | 109.1(4) |
| C(14)-C(15)-C(8) | 109.8(4) | C(66)-C(65)-C(64) | 108.9(5) |
| C(15)-C(16)-C(11) | 99.7(4) | C(65)-C(66)-C(61) | 99.3(4) |
| O(2X)-C(1X)-O(3X) | 123.7(5) | O(3Y)-C(1Y)-O(2Y) | 125.2(5) |
| O(2X)-C(1X)-C(4X) | 121.2(5) | O(3Y)-C(1Y)-C(4Y) | 116.1(5) |
| O(3X)-C(1X)-C(4X) | 115.1(5) | O(2Y)-C(1Y)-C(4Y) | 118.7(5) |
| O(5X)-C(4X)-C(6X) | 113.4(4) | O(5Y)-C(4Y)-C(6Y) | 112.3(4) |
| O(5X)-C(4X)-C(1X) | 114.0(4) | O(5Y)-C(4Y)-C(1Y) | 111.8(4) |
| C(6X)-C(4X)-C(1X) | 107.5(4) | C(6Y)-C(4Y)-C(1Y) | 112.7(4) |
| O(7X)-C(6X)-C(4X) | 112.0(4) | O(7Y)-C(6Y)-C(8Y) | 114.1(4) |
| O(7X)-C(6X)-C(8X) | 111.8(4) | O(7Y)-C(6Y)-C(4Y) | 113.9(4) |
| C(4X)-C(6X)-C(8X) | 113.7(4) | C(8Y)-C(6Y)-C(4Y) | 106.7(4) |
| O(10X)-C(8X)-O(9X) | 125.6(5) | O(10Y)-C(8Y)-O(9Y) | 123.7(5) |
| O(10X)-C(8X)-C(6X) | 119.3(5) | O(10Y)-C(8Y)-C(6Y) | 121.4(5) |
| O(9X)-C(8X)-C(6X) | 115.1(5) | O(9Y)-C(8Y)-C(6Y) | 114.9(5) |

TABLE XIX

Anisotropic Displacement Parameters (Å$^2$ × 10$^3$) For Form C.
(The Anisotropic displacement factor exponent takes the form:
$-2\pi2[h^2 a^{*2}U_{11} + \ldots + 2 h k a^* b^* U_{12}]$).

| | $U_{11}$ | $U_{22}$ | $U_{33}$ | $U_{23}$ | $U_{13}$ | $U_{12}$ |
|---|---|---|---|---|---|---|
| N(1) | 42(4) | 46(4) | 46(4) | −8(3) | 4(3) | 0(3) |
| C(2) | 53(5) | 51(5) | 52(5) | −5(4) | 9(4) | 3(4) |
| C(3) | 63(5) | 40(4) | 49(4) | −2(4) | 19(4) | 11(4) |
| N(4) | 59(4) | 30(3) | 37(3) | −8(3) | −7(3) | 11(3) |
| C(5) | 44(4) | 19(3) | 35(4) | 1(3) | −8(3) | 9(3) |
| C(6) | 27(3) | 25(4) | 39(4) | 1(3) | 3(3) | 3(3) |
| C(7) | 30(4) | 36(4) | 30(4) | −1(3) | −10(3) | 4(3) |
| C(8) | 28(4) | 27(3) | 19(3) | 1(2) | −4(3) | 3(3) |
| C(9) | 27(3) | 20(3) | 29(4) | 4(3) | −9(3) | 0(3) |
| C(10) | 33(4) | 32(4) | 44(4) | −8(3) | −14(3) | −4(3) |
| C(11) | 30(3) | 26(4) | 38(4) | 0(3) | −1(3) | −6(3) |
| C(12) | 22(3) | 44(4) | 34(3) | 0(3) | 0(3) | 0(3) |
| N(13) | 27(3) | 32(3) | 21(3) | 1(2) | 0(2) | 1(2) |
| C(14) | 26(3) | 34(4) | 27(3) | −4(3) | −11(3) | −1(3) |

TABLE XIX-continued

Anisotropic Displacement Parameters ($Å^2 \times 10^3$) For Form C.
(The Anisotropic displacement factor exponent takes the form:
$-2\pi 2[h^2 a^{*2}U_{11} + \ldots + 2 h k a^* b^* U_{12}]$).

| | $U_{11}$ | $U_{22}$ | $U_{33}$ | $U_{23}$ | $U_{13}$ | $U_{12}$ |
|---|---|---|---|---|---|---|
| C(15) | 24(3) | 29(4) | 30(3) | 7(3) | −5(3) | −2(3) |
| C(16) | 42(4) | 41(4) | 39(4) | 5(3) | 7(3) | −2(3) |
| C(1X) | 23(3) | 19(3) | 28(4) | −1(3) | 8(3) | 1(3) |
| O(2X) | 28(2) | 56(3) | 25(2) | −7(2) | −2(2) | −1(2) |
| O(3X) | 19(2) | 69(3) | 26(2) | 8(2) | 5(2) | 2(2) |
| C(4X) | 19(3) | 30(3) | 24(3) | 5(3) | −1(2) | 1(3) |
| O(5X) | 29(2) | 34(2) | 33(2) | 5(2) | −5(2) | 8(2) |
| C(6X) | 20(3) | 28(3) | 26(3) | −1(3) | 2(2) | 1(3) |
| O(7X) | 21(2) | 25(2) | 36(2) | −3(2) | 5(2) | 4(2) |
| C(8X) | 21(3) | 30(4) | 16(3) | −2(3) | 1(2) | 5(3) |
| O(9X) | 19(2) | 43(3) | 49(3) | −10(2) | −1(2) | 4(2) |
| O(10X) | 26(2) | 35(3) | 45(2) | −10(2) | −7(2) | −1(2) |
| O(1W) | 28(2) | 47(3) | 35(2) | −9(2) | 1(2) | −1(2) |
| N(51) | 29(3) | 47(4) | 54(4) | 7(3) | −3(3) | 8(3) |
| C(52) | 44(4) | 46(4) | 51(5) | 11(4) | −9(4) | 4(3) |
| C(53) | 50(5) | 48(4) | 35(4) | 2(3) | −4(3) | 10(4) |
| N(54) | 53(4) | 40(3) | 37(3) | 4(3) | 5(3) | 8(3) |
| C(55) | 34(4) | 28(3) | 27(3) | 5(3) | 4(3) | 3(3) |
| C(56) | 28(4) | 25(3) | 36(4) | −5(3) | 2(3) | 2(3) |
| C(57) | 30(4) | 34(4) | 32(4) | 4(3) | 7(3) | 3(3) |
| C(58) | 32(4) | 24(4) | 24(3) | −1(3) | 5(3) | −1(3) |
| C(59) | 22(3) | 21(3) | 33(4) | 0(3) | 1(3) | −2(3) |
| C(60) | 25(3) | 32(4) | 49(4) | 3(3) | 10(3) | −3(3) |
| C(61) | 26(3) | 30(4) | 40(4) | 2(3) | −6(3) | −6(3) |
| C(62) | 25(3) | 35(4) | 38(4) | 4(3) | 0(3) | −2(3) |
| N(63) | 25(3) | 27(3) | 27(3) | −2(2) | 5(2) | 1(2) |
| C(64) | 36(3) | 33(4) | 18(3) | 2(3) | 8(3) | 1(3) |
| C(65) | 35(3) | 33(4) | 21(3) | −5(3) | 3(3) | 6(3) |
| C(66) | 42(4) | 32(4) | 33(4) | −6(3) | −6(3) | 2(3) |
| C(1Y) | 23(3) | 38(4) | 17(3) | −1(3) | −6(2) | 0(3) |
| O(2Y) | 21(2) | 42(3) | 43(2) | 11(2) | 5(2) | −2(2) |
| O(3Y) | 19(2) | 41(3) | 44(3) | 11(2) | 3(2) | 8(2) |
| C(4Y) | 18(3) | 22(3) | 21(3) | 3(2) | −1(2) | 4(3) |
| O(5Y) | 21(2) | 31(2) | 30(2) | 3(2) | −2(2) | 4(2) |
| C(6Y) | 23(3) | 30(3) | 17(3) | 4(3) | 1(2) | 7(3) |
| O(7Y) | 32(2) | 37(3) | 31(3) | −3(2) | 6(2) | 7(2) |
| C(8Y) | 23(3) | 16(3) | 33(4) | 3(3) | −2(3) | −4(2) |
| O(9Y) | 19(2) | 61(3) | 27(2) | −9(2) | −6(2) | 5(2) |
| O(10Y) | 28(2) | 57(3) | 24(2) | 4(2) | 6(2) | 1(2) |
| O(2W) | 32(2) | 50(3) | 35(3) | 7(2) | −2(2) | 3(2) |

TABLE XX

Hydrogen Coordinates ($\times 10^4$) And Isotropic Displacement Parameters ($Å^2 \times 10^3$) For Form C.

| | x | y | z | U(eq) |
|---|---|---|---|---|
| H(2) | −1359 | 10366 | 435 | 80 |
| H(3) | 1066 | 10546 | 2094 | 80 |
| H(7) | 732 | 9899 | −4690 | 80 |
| H(10) | 5770 | 10272 | −1377 | 80 |
| H(11) | 7541 | 10086 | −4476 | 80 |
| H(12A) | 7896 | 9284 | −4990 | 80 |
| H(12B) | 7499 | 9383 | −3021 | 80 |
| H(13X) | 5710(100) | 8750(30) | −4290(90) | 80 |
| H(13Y) | 4660(100) | 9130(30) | −3380(100) | 80 |
| H(14A) | 3147 | 9025 | −5797 | 80 |
| H(14B) | 4897 | 9035 | −6903 | 80 |
| H(15) | 3202 | 9720 | −7264 | 80 |
| H(16A) | 5715 | 10190 | −6996 | 80 |
| H(16B) | 6570 | 9712 | −7324 | 80 |
| H(3XX) | −980(110) | 7490(30) | −4900(90) | 80 |
| H(4X) | 4082 | 7208 | −5730 | 80 |
| H(5XX) | 3350(100) | 7550(30) | −2600(100) | 80 |
| H(6X) | 4144 | 7936 | −6589 | 80 |
| H(7XX) | 3230(100) | 8210(30) | −3240(100) | 80 |
| H(1WX) | 2060(110) | 8070(30) | −390(90) | 80 |
| H(1WY) | 4280(110) | 8050(30) | −270(100) | 80 |
| H(52) | 4720 | 6106 | 5423 | 80 |

TABLE XX-continued

Hydrogen Coordinates ($\times 10^4$) And Isotropic Displacement Parameters ($Å^2 \times 10^3$) For Form C.

| | x | y | z | U(eq) |
|---|---|---|---|---|
| H(53) | 2329 | 5927 | 7019 | 80 |
| H(57) | 2559 | 6605 | 286 | 80 |
| H(60) | −2435 | 6220 | 3610 | 80 |
| H(61) | −4250 | 6416 | 511 | 80 |
| H(62A) | −4647 | 7211 | 87 | 80 |
| H(62B) | −4158 | 7101 | 2035 | 80 |
| H(63X) | −2480(100) | 7730(30) | 650(90) | 80 |
| H(63Y) | −1300(100) | 7360(30) | 1730(100) | 80 |
| H(64A) | 141 | 7470 | −772 | 80 |
| H(64B) | −1620 | 7471 | −1889 | 80 |
| H(65) | 16 | 6777 | −2307 | 80 |
| H(66A) | −2509 | 6308 | −2010 | 80 |
| H(66B) | −3358 | 6788 | −2329 | 80 |
| H(4Y) | −860 | 8553 | −1607 | 80 |
| H(5YX) | −140(100) | 8240(30) | 1670(100) | 80 |
| H(6Y) | −797 | 9286 | −757 | 80 |
| H(7YX) | −100(110) | 9020(30) | 2280(100) | 80 |
| H(9YX) | 4230(110) | 8990(30) | 40(90) | 80 |
| H(2WX) | 1040(110) | 8370(30) | 4630(100) | 80 |
| H(2WY) | −990(110) | 8380(30) | 4830(100) | 80 |

Figure 4A:
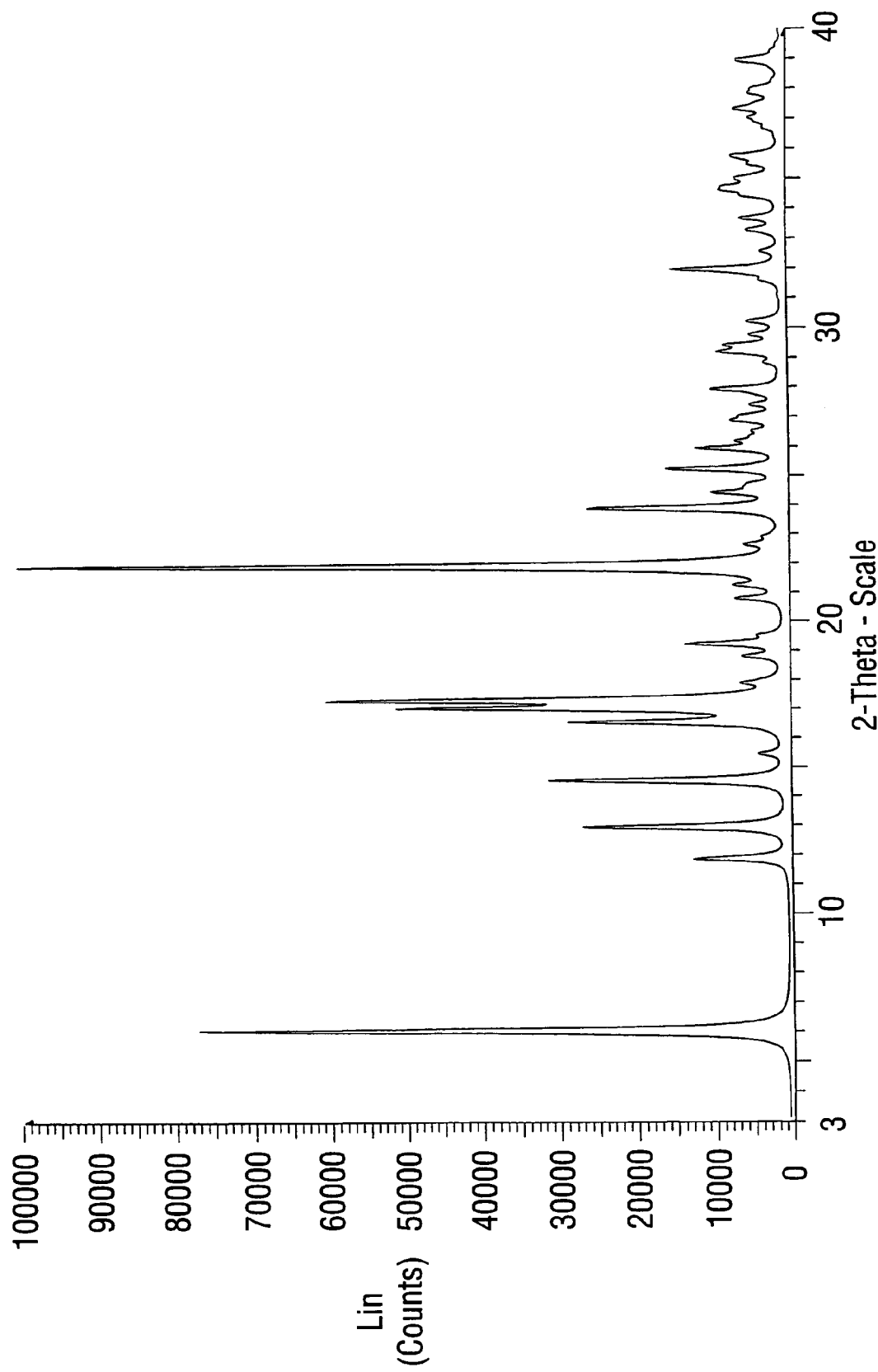
FIG. 4A is the calculated powder X-ray diffraction pattern of the anhydrous Form B L-tartrate salt of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

The powder X-ray diffraction patterns for Forms B and C were calculated from the respective single crystal data gathered for each L-tartrate salt form via the use of the XFOG and XPOW computer programs provided as part of the SHELXL™ computer library. The calculated powder pattern for Form B is shown in FIG. 4A. The calculated powder pattern for Form C is shown in FIG. 4B.

Figure 5A:
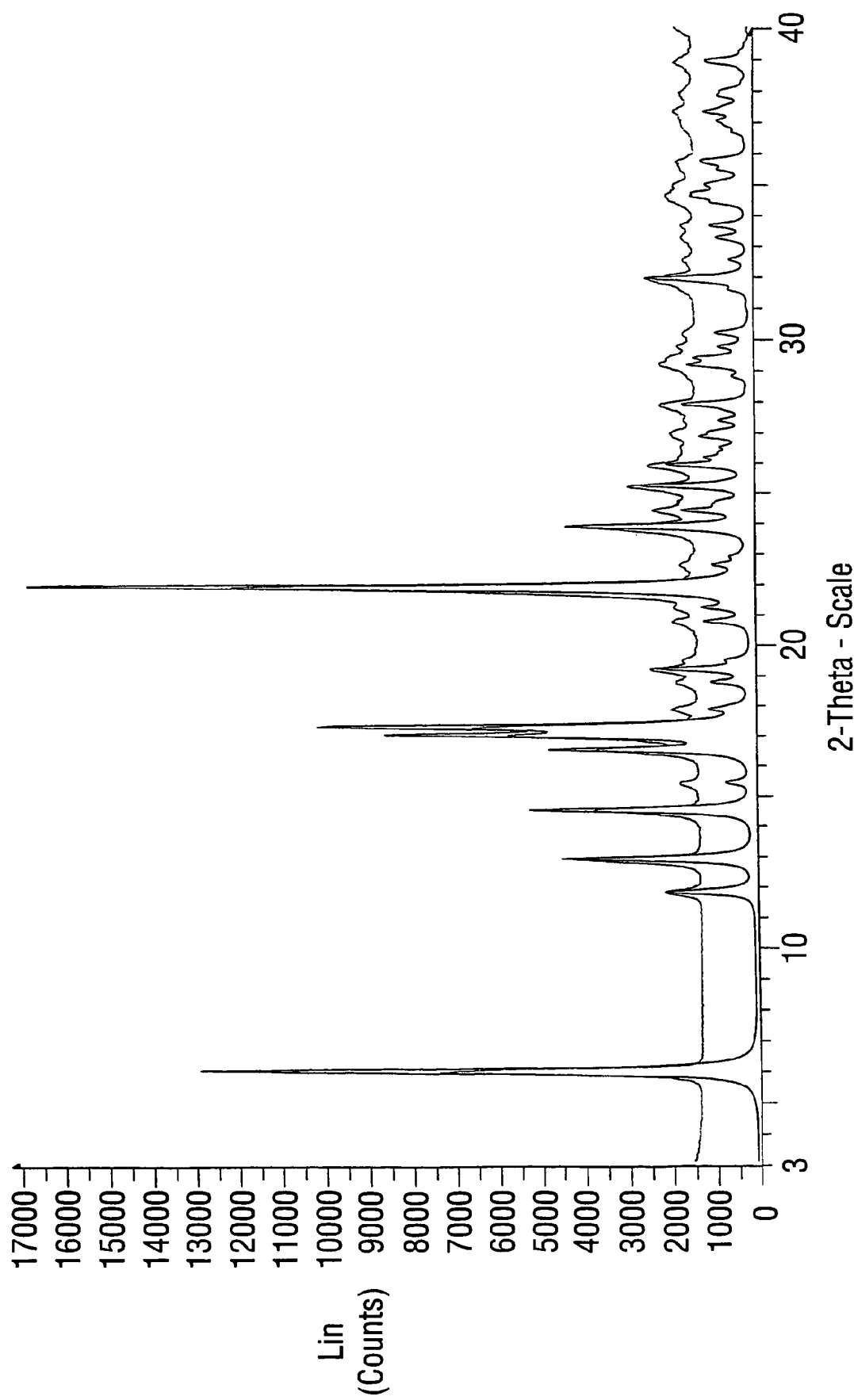
FIG. 5A is the calculated powder X-ray diffraction pattern (lower trace) laid over the observed X-ray diffraction pattern (upper trace) for the anhydrous Form B L-tartrate salt of 5,8,14-triazatetra-cyclo[10.3.1.0$^{2,11}$.0$^{4,9}$-hexadeca-2(11),3,5,7,9]-pentaene (y axis is linear counts per second; X in degrees 2 theta).

A comparison of the observed Form B powder pattern and the calculated pattern results are displayed in the overlaid powder X-ray diffraction pattern of FIG. 5A. The lower pattern trace corresponds to the calculated powder pattern (from single crystal results) and the upper pattern corresponds to a representative experimental powder pattern. The general match between the two patterns indicates the agreement between powder sample and the corresponding single crystal structure.

Figure 5B:
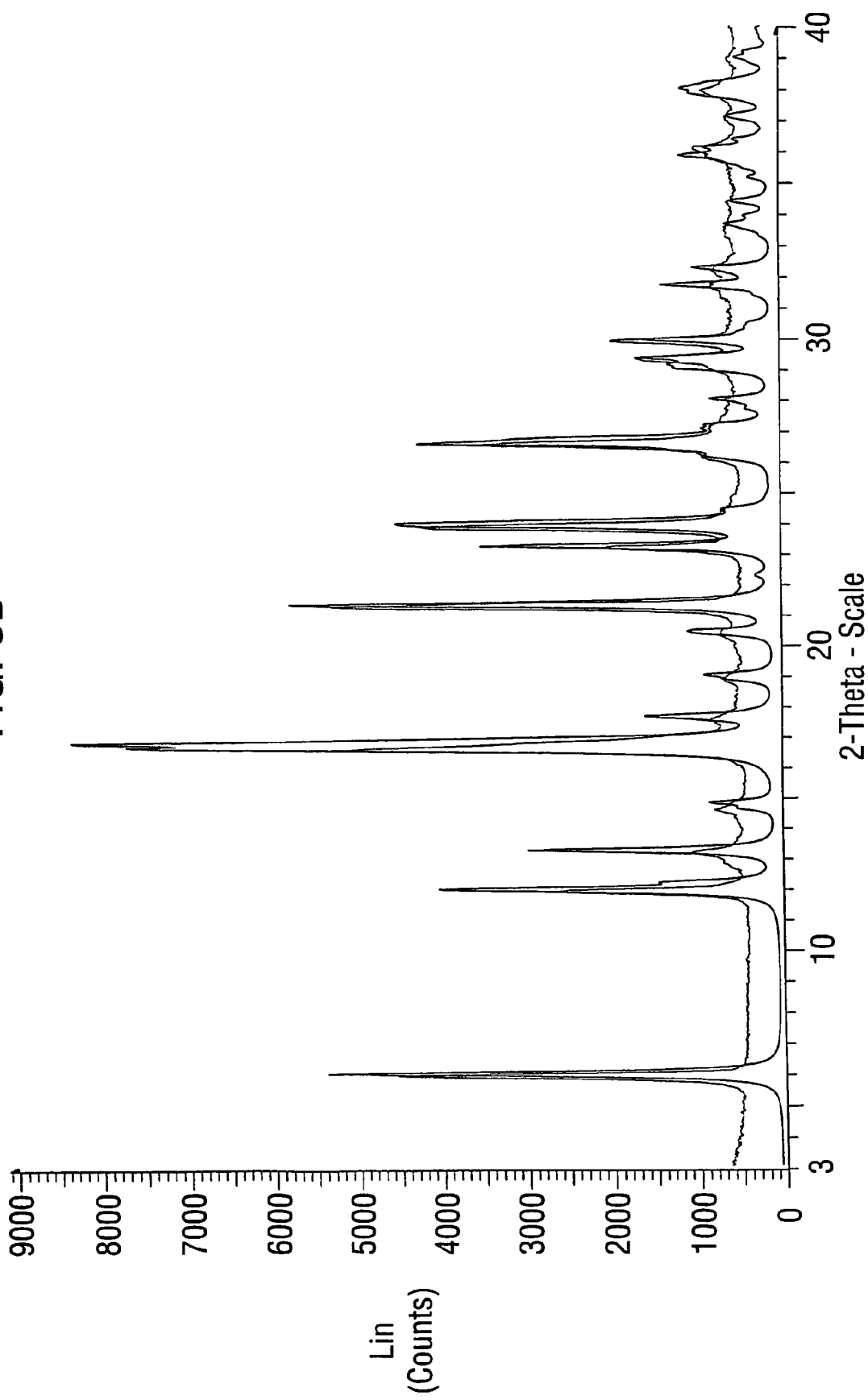
FIG. 5B is the calculated powder X-ray diffraction pattern (lower trace) laid over the observed X-ray diffraction pattern (upper trace) for the Form C L-tartrate salt hydrate of 5,8,14-triazatetra-cyclo[10.3.1.0$^{2,11}$.0$^{4,9}$]-hexadeca-2(11),3,5,7,9-pentaene (y axis is linear counts per second; X in degrees 2 theta).

A comparison of the observed Form C powder pattern and the calculated pattern results are displayed in the overlaid powder X-ray diffraction pattern of FIG. 5B. The lower pattern trace corresponds to the calculated powder pattern (from single crystal results) and the upper pattern corresponds to a representative experimental powder pattern. The general match between the two patterns indicates the agreement between powder sample and the corresponding single crystal structure.

Solid State NMR

Forms A, B and C of the L-tartrate salt of 5,8,14-triazatetracyclo[10.3.1.0$^{2,11}$.0$^{4,9}$]-hexadeca-2(11),3,5,7,9-pentaene were characterized by solid state NMR techniques. Approximately 300 mg of a sample was tightly packed into 7 mm ZrO spinner. The $^{13}$C spectra were collected using cross-polarization magic angle spinning (CPMAS) at 295 K on Bruker 7 mm WB MAS probe positioned into a widebore Bruker Avance DRX 500 MHz NMR spectrometer. The samples were spun at 7 kHz. The cross-polarization contact time was set to 1 ms. The total of 512 scans were acquired for most of the samples resulting in approximately 30 minute acquisition times. The spectra were referenced using external sample of adamantane with the most upfield methyl signal set to 29.5 ppm.

Figure 7A:
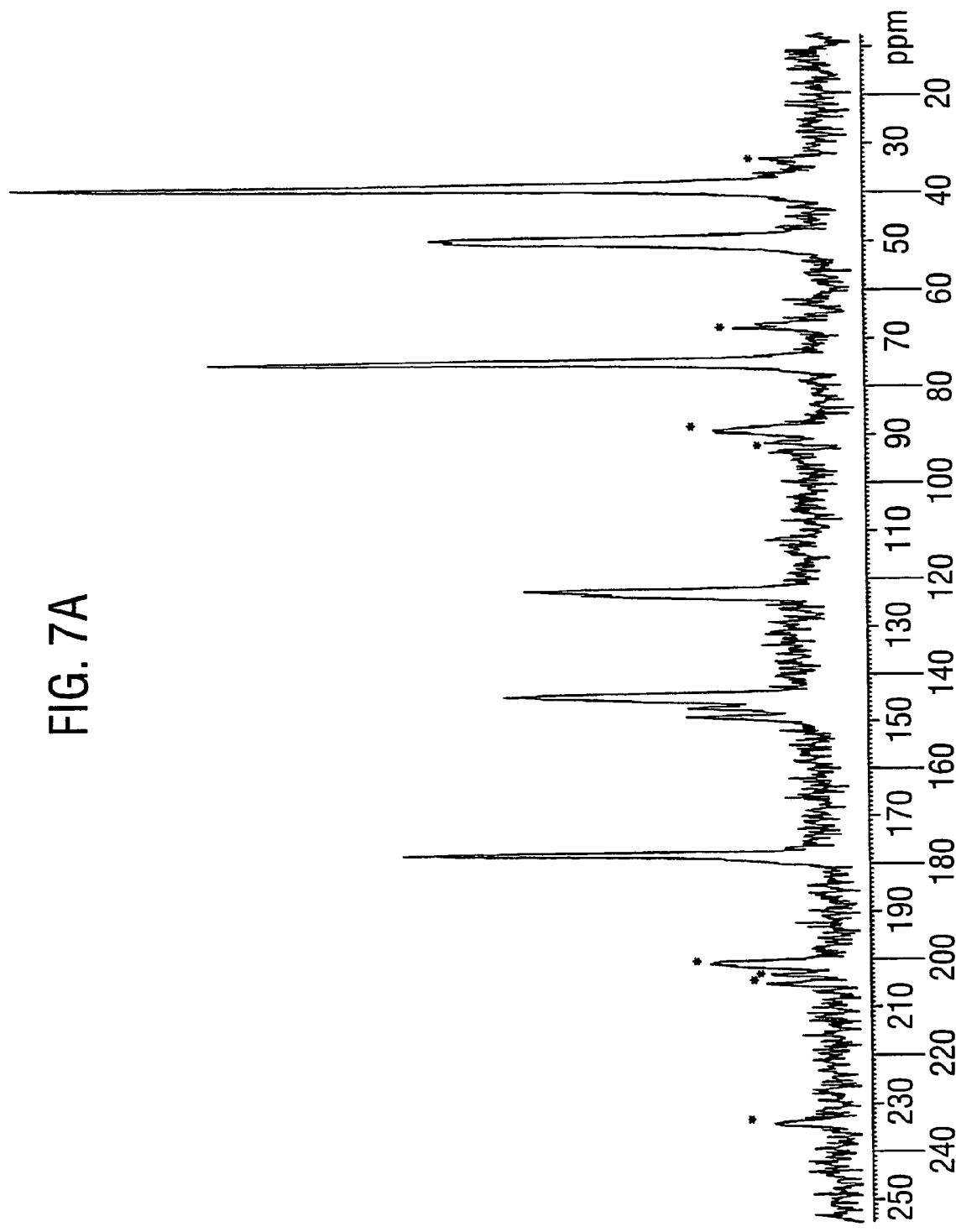
FIGS. 7A, 7B and 7C are the solid state $^{13}$C NMR spectra of the L-tartrate salts of 5,8,14-triazatetra-cyclo[10.3.1.0$^{2,11}$.0$^{4,9}$]-hexadeca-2(11),3,5,7,9-pentaene Forms A, B and C, respectively, as measured by cross-polarization magic angle spinning (CPMAS) at 295 K on a Bruker 7 mm wide-bore magic angle spinning (WB MAS) probe positioned in a Bruker Avance DRX 500 MHz NMR Spectrometer. Peaks marked with asterisks (*) are spinning sidebands which are displaced at multiples of the spinning frequencies along both sides of the real peaks (centerbands).
Figure 7B:
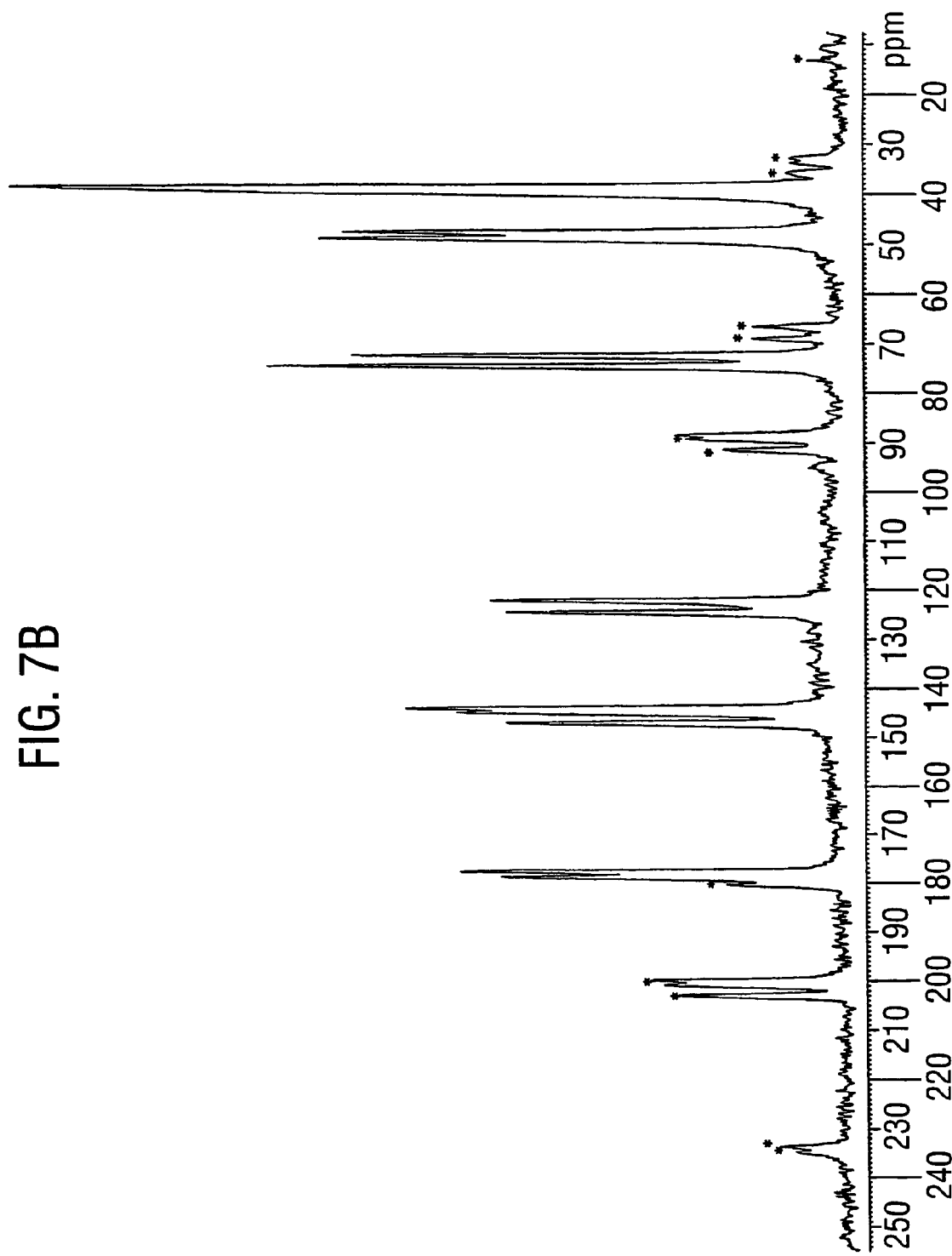
Figure 7C:
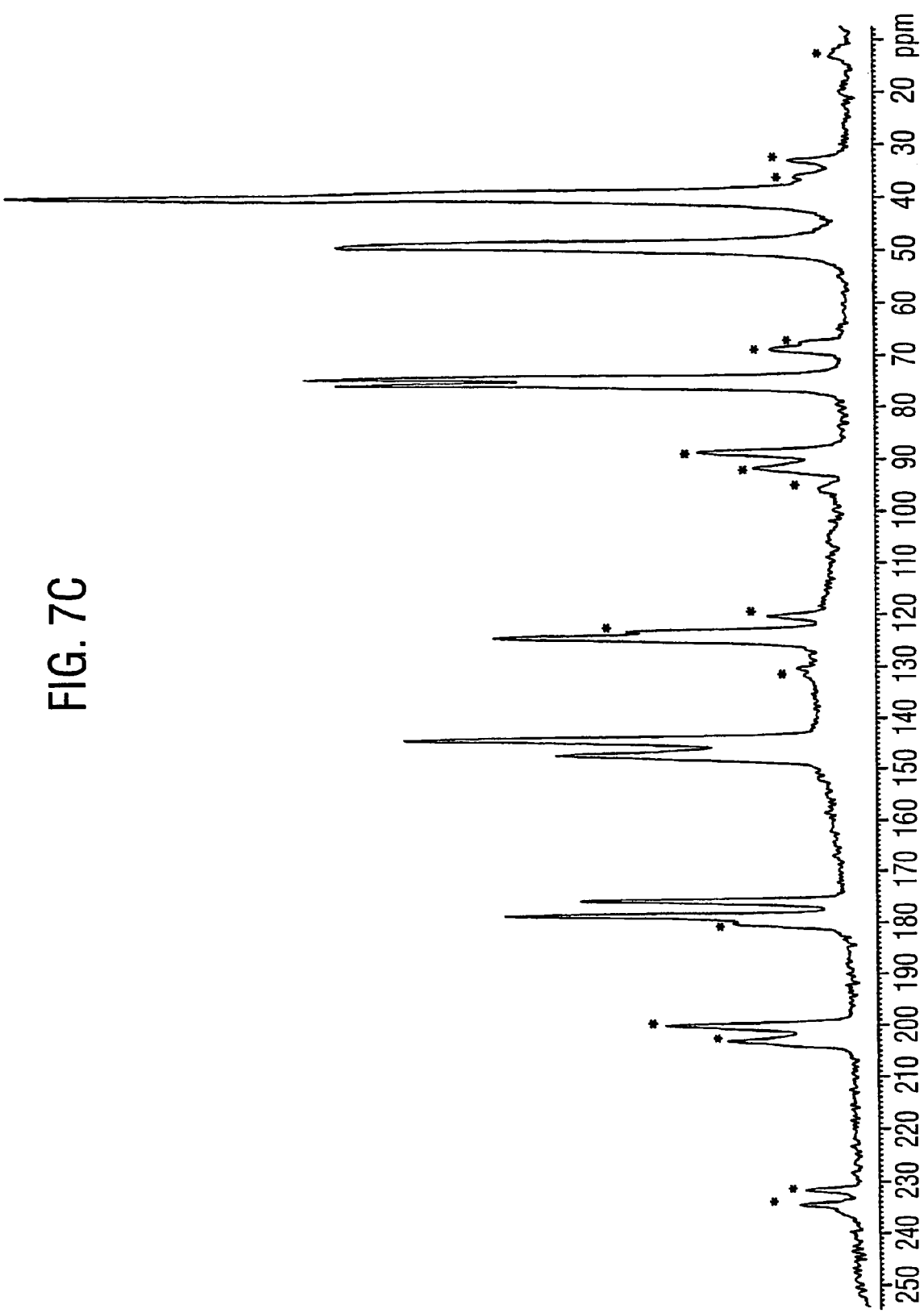

The resulting $^{13}$C CPMAS spectra of Forms A, B and C are shown in FIGS. 7A, 7B and 7C, respectively. The samples behaved reasonably well from the point of view of solid state spectra quality. The resolution was good and the sensitivity was acceptable. The spectra features of all the compounds differ substantially from each other suggesting that solid state NMR can easily resolve the minor physical/chemical differences between the samples.

All the peaks marked with asterisks (*) are spinning sidebands in FIGS. 7A, 7B and 7C. The spinning sidebands are displaced at multiple of the spinning frequencies along both sides of the real peaks (centerbands). The spinning speed was set to 7 kHz which at the 500 MHz magnet translates into 55.7 ppm. The sideband intensities depend on the spinning speed (the higher the speed the lower the sideband intensity) and on the size of the anisotropic contribution of the chemical shielding for the given carbon. They can be easily distinguished from centerbands by variable spinning speed experiments. Carbonyl and aromatic sites tend to have very intense sidebands due to their large chemical shielding anisotropies. CH and $CH_2$ type of carbons give origin to relatively small spinning sidebands. Methyl groups ($CH_3$) usually don't generate any sidebands.

The major resonance peaks (those downfield from 100 ppm; ±0.1 ppm) for the solid state carbon spectrum of 5,8,14-triazatetracyclo[$10.3.1.0^{2,11}.0^{4,9}$]-hexadeca-2(11),3,5,7,9-pentaene L-tartrate salt Forms A, B and C are listed in Table XXI.

TABLE XXI

Major Solid State $^{13}$C-NMR Resonance Peaks For 5,8,14-triazatetracyclo[$10.3.1.0^{2,11}.0^{4,9}$]-hexadeca-2(11),3,5,7,9-pentaene L-Tartrate Salt Forms A, B and C (Only Peaks Downfield from 100 ppm Listed) (Adamantane 29.5 ppm Standard).

| FORM A $^{13}$C (ppm) Solid | FORM B $^{13}$C (ppm) Solid | FORM C $^{13}$C (ppm) Solid |
|---|---|---|
| 178.4 | 179.2 | 179.0 |
| 149.3 | 178.0 | 176.1 |
| 147.4 | 147.4 | 147.5 |
| 145.1 | 145.2 | 144.5 |
| 122.9 | 144.4 | 124.6 |
|  | 124.8 |  |
|  | 122.5 |  |

The L-tartrate, the D-tartrate, the D,L-tartrate and the meso-tartrate salts of the invention (hereafter "the active salts") can be administered via either the oral, transdermal (e.g., through the use of a patch), intranasal, sublingual, rectal, parenteral or topical routes. Transdermal and oral administration are preferred. These salts are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active salts can be administered alone or in combination with pharmaceutically acceptable carriers or diluents by any of the several routes previously indicated. More particularly, the active salts can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compound is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active salts topically and this can be done by way of creams, a patch, jellies, gels, pastes, ointments and the like, in accordance with standard pharmaceutical practice.

EXAMPLES

The following examples illustrate the methods and compounds of the present invention. It will be understood, however, that the invention is not limited to the specific Examples.

Example 1

L-Tartrate Salt of 5,8,14-Triazatetracyclo[10.3.1.0$^{2,11}$.0$^{4,9}$]-hexadeca-2(11),3,5,7,9-pentaene (Anhydrous Polymorph, Form B)

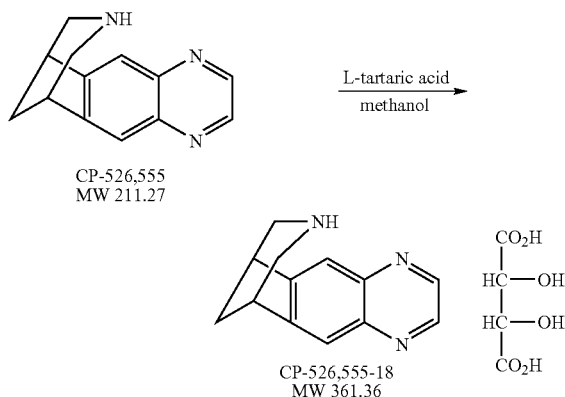

A speck-free vessel was charged with L-tartaric acid (780 grams, 1.1 equiv.) and methanol (7.5 L). The contents of the vessel were stirred until solution and speck free filtered into the crystallization vessel. 5,8,14-triazatetracyclo[10.3.1.0$^{2,11}$.0$^{4,9}$]-hexadeca-2(11),3,5,7,9-pentaene free base (992 grams) and methanol (7.5 L) were dissolved in the vessel; the mixture was maintained at between 20 to 25° C. The solution of 5,8,14-triazatetracyclo[10.3.1.0$^{2,11}$.0$^{4,9}$]-hexadeca-2(11),3,5,7,9-pentaene free base was added over about 45 minutes to the L-tartaric acid solution through a filter to render the solution speck and fiber free. The product was allowed to stir at 20 to 25° C. overnight and isolated by filtration. The product was dried under vacuum at 35 to 45° C. to give 1618.4 grams (95.4%) of 5,8,14-triazatetracyclo[10.3.1.0$^{2,11}$.0$^{4,9}$]-hexadeca-2(11),3,5,7,9-pentaene L-tartrate salt Form B (MW 361.36). M.p. 210.5° C.; verified as Form B by powder x-ray diffraction.

Example 2

L-Tartrate Salt of 5,8,14-Triazatetracyclo[10.3.1.0$^{2,11}$.0$^{4,9}$]-hexadeca-2(11),3,5,7,9-pentaene (Anhydrous Polymorph, Form A)

A reactor was charged with 5,8,14-triazatetracyclo[10.3.1.0$^{2,11}$.0$^{4,9}$]-hexadeca-2(11),3,5,7,9-pentaene free base (2 g; 0.0095 mole, 1.0 equiv.) and methanol (60 mL, 30 mL/g). The mixture was stirred at 20 to 25° C. until completely dissolved. A second reactor containing a solution of L-tartaric acid (1.55 g, 0.0103 mole, 1.1 equiv.) dissolved in methanol (60 mL, 30 mL/g) was heated to reflux in methanol (i.e., 60 to 66° C.). The free base solution was added to the L-tartaric acid solution at methanolic reflux temperature over 20 minutes. The resulting slurry was cooled to 20 to 25° C. over a 1 hour period. The reaction mixture was allowed to stir for approximately 2 hours followed by isolation of the product by filtration. The solid product was washed with methanol (10 mL), then dried under vacuum at 30 to 35° C. to give 3.3 grams (97%) of 5,8,14-triazatetracyclo[10.3.1.0$^{2,11}$.0$^{4,9}$]-hexadeca-2(11),3,5,7,9-pentaene L-tartrate Form A. The identity as Form A was determined by PXRD as compared with standard samples.

Example 3

L-Tartrate Salt Form C of 5,8,14-Triazatetracyclo[10.3.1.0$^{2,11}$.0$^{4,9}$]-hexadeca-2(11),3,5,7,9-pentaene (Form C)

Preparation of CP-526,555-18 Form C from Form A or Form B: L-tartrate salt Form B (~5 g) was dissolved in water (10 to 15 ml). Acetonitrile (200 to 300 ml) was added and Form C formed as a white precipitate. The resulting slurry was allowed to stir for 10 minutes and then filtered. The wet cake was then allowed to air dry. Product was determined to be Form C by NIR spectroscopy, DSC and PXRD analysis. This procedure may be run with Form A to yield Form C.

Example 4

L-Tartrate Salt Form A of 5,8,14-Triazatetracyclo[10.3.1.0$^{2,11}$.0$^{4,9}$]-hexadeca-2(11),3,5,7,9-pentaene (Form A)

Preparation of Form A from Form C: L-tartrate salt Form C (~2 g) was added to 200 to 300 mL hot ethanol (~75° C.) and allowed to stir for 30 minutes. The sample was filtered hot and then dried in a 45° C. vacuum oven (house vacuum). The material was determined to be Form A by NIR spectroscopy, DSC, and PXRD analysis.

What is claimed is:

1. The anhydrous L-tartrate salt of 5,8,14-triazatetracyclo[10.3.1.0$^{2,11}$.0$^{4,9}$]-hexadeca-2(11),3,5,7,9-pentaene, characterized substantially by at least one of the following powder x-ray diffraction pattern peaks expressed in term of 2θ as measured with copper radiation chosen from: 6.1, 16.8 and 21.9.

2. A compound according to claim 1 characterized substantially by the following principal powder x-ray diffraction pattern peaks expressed in terms of 2θ and d-spacings as measured with copper radiation:

| Angle 2θ | d-value (Å) |
|---|---|
| 6.1 | 14.5 |
| 12.2 | 7.2 |
| 13.0 | 6.8 |
| 14.7 | 6.0 |
| 16.8 | 5.3 |
| 19.4 | 4.6 |
| 21.9 | 4.1 |
| 24.6 | 3.6. |

3. A compound according to claim 1 characterized substantially by solid state $^{13}$C NMR resonance peaks at 178.4, 145.1, and 122.9 ppm.

4. The anhydrous L-tartrate salt of 5,8,14-triazatetracyclo[10.3.1.0$^{2,11}$0.$^{4,9}$]-hexadeca-2(11),3,5,7,9-pentaene, characterized substantially by at least one of the following powder x-ray diffraction pattern peaks expressed in terms of 2θ as measured with copper radiation chosen from: 5.9 and 21.8.

5. A compound according to claim 4 characterized substantially by the principal powder x-ray diffraction pattern peaks in terms of 2θ and d-spacings measured with copper radiation:

| Angle 2θ | d-value (Å) |
|---|---|
| 5.9 | 15.0 |
| 12.8 | 6.9 |
| 14.4 | 6.1 |
| 15.3 | 5.8 |
| 16.9 | 5.2 |
| 17.2 | 5.2 |
| 21.8 | 4.1 |
| 23.8 | 3.7 |
| 25.1 | 3.5 |

6. A compound according to claim 4 characterized substantially by the solid state $^{13}$C NMR principal resonance peaks at: 179.2, 178.0, 144.4, 124.8 and 122.5 ppm.

7. The L-tartrate hydrate salt of 5,8,14-triazatetracyclo [10.3.1 $0^{2,11}$ $0^{4,9}$]-hexadeca-2(11),3,5,7,9-pentaene, characterized substantially by at least one of the following powder x-ray diffraction pattern peaks expressed in terms of 2θ as measured with copper radiation chosen from: 11.8, 16.5, 23.1 and 26.5.

8. A compound according to claim 7 characterized substantially by the principal powder x-ray diffraction pattern peaks in terms of 2θ and d-spacings as measured with copper radiation:

| Angle 2θ (±0.2) | d-value (Å) (±0.2) |
|---|---|
| 5.9 | 15.1 |
| 11.8 | 7.5 |
| 16.5 | 5.4 |
| 21.2 | 4.2 |
| 23.1 | 3.8 |
| 23.8 | 3.7 |
| 26.5 | 3.4. |

9. A compound according to claim 7 characterized substantially by solid state $^{13}$C NMR principal resonance peaks: 179.0, 176.1, 147.5 and 144.5 ppm.

10. A pharmaceutical composition comprising a pharmaceutically acceptable carrier and a compound according to claim 1.

11. A pharmaceutical composition comprising a pharmaceutically acceptable carrier and a compound according to claim 4.

12. A pharmaceutical composition comprising a pharmaceutically acceptable carrier and a compound according to claim 7.

13. A method of treatment for nicotine dependency, addiction and withdrawal comprising the administration of a compound according to claim 1 to a subject in need thereof.

14. A method of treatment for nicotine dependency, addiction and withdrawal comprising the administration of a compound according to claim 4 to a subject in need thereof.

15. A method of treatment for nicotine dependency, addiction and withdrawal comprising the administration of a compound according to claim 7 to a subject in need thereof.

* * * * *

UNITED STATES PATENT AND TRADEMARK OFFICE
CERTIFICATE OF CORRECTION

PATENT NO. : 7,265,119 B2 Page 1 of 1
APPLICATION NO. : 11/069724
DATED : September 4, 2007
INVENTOR(S) : Bogle et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 105 days Delete the phrase "by 105 days" and insert -- by 89 days --

Signed and Sealed this

Eighth Day of April, 2008

JON W. DUDAS
*Director of the United States Patent and Trademark Office*